(12) United States Patent
Stupple

(10) Patent No.: US 7,790,740 B2
(45) Date of Patent: Sep. 7, 2010

(54) IMIDAZOPYRIDINE SUBSTITUTED TROPANE DERIVATIVES WITH CCR5 RECEPTOR ANTAGONIST ACTIVITY FOR THE TREATMENT OF HIV AND INFLAMMATION

(75) Inventor: Paul Anthony Stupple, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 11/845,500

(22) Filed: Aug. 27, 2007

(65) Prior Publication Data

US 2008/0045563 A1    Feb. 21, 2008

Related U.S. Application Data

(62) Division of application No. 10/953,136, filed on Sep. 28, 2004, now Pat. No. 7,309,790.

(60) Provisional application No. 60/512,307, filed on Oct. 17, 2003, provisional application No. 60/527,545, filed on Dec. 5, 2003.

(30) Foreign Application Priority Data

Oct. 3, 2003  (GB) ................ 0323236.0
Oct. 27, 2003  (GB) ................ 0325020.6
Aug. 19, 2004  (GB) ................ 0418566.6

(51) Int. Cl.
*A61K 31/44* (2006.01)
*C07D 471/02* (2006.01)
(52) U.S. Cl. ................... 514/303; 546/118
(58) Field of Classification Search ........... 514/303; 546/118
See application file for complete search history.

(56) References Cited

U.S. PATENT DOCUMENTS 6,106,864 A    8/2000   Dolan et al.

FOREIGN PATENT DOCUMENTS

| WO | WO 91/11172 | 8/1991 |
| WO | WO 94/02518 | 2/1994 |
| WO | WO 98/55148 | 12/1998 |
| WO | WO 00/35298 | 6/2000 |

OTHER PUBLICATIONS

Cascieri, M., et al., "The Chemokine/Chemokine Receptor Family: Potential And Progress For Therapeutic Intervention," *Curr. Opin. Chem. Biol.*, 2000, 420-427, vol. 4, No. 4.

Cavero, I., et al., "Drugs That Prolong QT Interval As An Unwanted Effect: Assessing Their Liikelihood Of Inducing Hazardous Cardiac Dysryhthmias," *Expert Opinion Of Pharmacotherapy*, 2000, 947-973, vol. 1, No. 5.

Combadiere, C., et al., "Cloning And Functional Expression Of CC CKR5, A Human Monocyte CC Chemokine Receptor Selective for MIP-1α, MIP-1β, And RANTES," *Journal of Leukocyte Biology*, 1996, 147-152, vol. 60.

Finnin, B., et al., "Transdermal Penetration Enhancers: Applications, Limitations, And Potential," *Journal Of Pharmaceutical Sciences*, 1999, 955-958, vol. 88, No. 10.

Green, T., et al., *Protective Groups In Organic Synthesis'*, 3rd Edition, 1999, 494-653, John Wiley and Sons.

Haleblian, J., "Characterization Of Habits And Crystalline Modification Of Solids And Their Pharmaceutical Applications," *Journal of Pharmaceutical Science*, 1975, 1269-1288, vol. 64, No. 8.

Liang, et al., "Fast-Dissolving Intraoral Drug Delivery Systems," *Expert Opinion in Therapeutic Patents*, 2001, 981-986, vol. 11, No. 6.

March, J., *Advanced Organic Chemistry*, 4th Edition, 1992, 352, Wiley Interscience.

March, J., *Advanced Organic Chemistry*, 4th Edition, 1992, 652, Wiley Interscience.

Verma, et al., "Pharmaceutical Technology On-Line", 2001, 1-14, vol. 25, No. 2.

*Primary Examiner*—Taylor Victor Oh
(74) *Attorney, Agent, or Firm*—Jennifer Kispert; J. Michael Dixon

(57) ABSTRACT

The present invention provides compounds of formula (I)

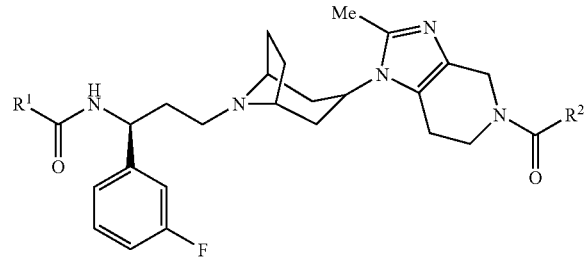

(I)

wherein $R^1$ and $R^2$ are as defined hereinabove.

The compounds of the present invention are modulators, especially antagonists, of the activity of chemokine CCR5 receptors. Modulators of the CCR5 receptor may be useful in the treatment of various inflammatory diseases and conditions, and in the treatment of infection by HIV and genetically related retroviruses.

10 Claims, No Drawings

IMIDAZOPYRIDINE SUBSTITUTED TROPANE DERIVATIVES WITH CCR5 RECEPTOR ANTAGONIST ACTIVITY FOR THE TREATMENT OF HIV AND INFLAMMATION

This application claims the benefit of United Kingdom Application No. GB0323236.0, filed Oct. 3, 2003; United Kingdom Application No. GB0325020.6, filed Oct. 27, 2003; United Kingdom Application No. GB0418566.6, filed Aug. 19, 2004; U.S. patent application Ser. No. 10/953,136 filed on Sep. 28, 2005; U.S. Provisional Application Ser. No. 60/512,307, filed Oct. 17, 2003; and U.S. Provisional Application Ser. No. 60/527,545 filed Dec. 5, 2003, the contents of which are all hereby incorporated by reference in their entirety.

FIELD OF THE INVENTION

This invention relates to tropane derivatives, to processes for their preparation, to compositions containing them and to their use.

More particularly, the present invention relates to the use of 8-azabicyclo[3.2.1]octane derivatives in the treatment of a variety of disorders, including those in which the modulation, in particular antagonism, of chemokine CCR5 receptors is implicated. Accordingly, compounds of the invention are useful in the treatment of HIV, such as HIV-1, and genetically related retroviral infections (and the resulting acquired immune deficiency syndrome, AIDS), and inflammatory diseases.

BACKGROUND OF THE INVENTION

The name "chemokine", is a contraction of "chemotactic cytokines". The chemokines comprise a large family of proteins which have in common important structural features and which have the ability to attract leukocytes. As leukocyte chemotactic factors, chemokines play an indispensable role in the attraction of leukocytes to various tissues of the body, a process which is essential for both inflammation and the body's response to infection. Because chemokines and their receptors are central to the pathophysiology of inflammatory and infectious diseases, agents which are active in modulating, preferably antagonising, the activity of chemokines and their receptors, are useful in the therapeutic treatment of such inflammatory and infectious diseases.

The chemokine receptor CCR5 is of particular importance in the context of treating inflammatory and infectious diseases. CCR5 is a receptor for chemokines, especially for the macrophage inflammatory proteins (MIP) designated MIP-1α and MIP-1β, and for a protein which is regulated upon activation and is normal T-cell expressed and secreted (RANTES).

We have now found a group of compounds that are both potent and selective modulators, in particular antagonists, of the CCR5 receptor.

SUMMARY OF THE INVENTION

According to a first aspect of the present invention, there is provided a compound of formula (I)

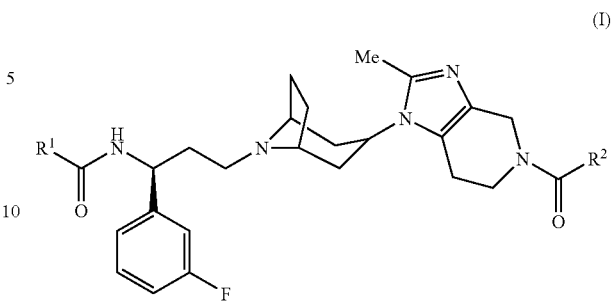

or a pharmaceutically acceptable salt, solvate of derivative thereof, wherein:
$R^1$ is $C_1$-$C_6$ alkyl; and
$R^2$ is $C_1$-$C_6$ alkyl or $C_3$-$C_7$ cycloalkyl, wherein said $C_1$-$C_6$ alkyl is optionally substituted by $CF_3$.

The term "alkyl" as a group or part of a group includes straight chain and branched groups. Examples of alkyl include methyl, ethyl, n-propyl, i-propyl, n-butyl, i-butyl, sec-butyl and t-butyl. The term "$C_3$-$C_7$ cycloalkyl" means cyclopropyl, cyclobutyl, cyclopentyl, cyclohexyl or cycloheptyl.

In one embodiment, $R^1$ is $C_1$-$C_4$alkyl.
In a further embodiment, $R^1$ is methyl.
In a further embodiment, $R^2$ is $C_1$-$C_4$alkyl optionally substituted by $CF_3$.
In a further embodiment, $R^2$ is cyclopropyl or cyclobutyl.
In a further embodiment, $R^2$ is methyl, ethyl or i-propyl.

It is to be understood that the invention covers all combinations of embodiments of the invention as described hereinabove, consistent with the definition of compounds of formula (I).

DETAILED DESCRIPTION OF THE INVENTION AND PREFERRED EMBODIMENTS

The compounds of the invention include compounds of formula (I) and pharmaceutically acceptable salts, solvates or derivatives thereof (wherein derivatives include complexes, prodrugs and isotopically-labelled compounds, as well as salts and solvates thereof). In a further embodiment, the compounds of the invention are the compounds of formula (I) and pharmaceutically acceptable salts and solvates thereof, in particular the compounds of formula (I). It is to be understood that the aforementioned compounds of the invention include polymorphs and isomers thereof.

Pharmaceutically acceptable salts of the compounds of formula (I) include the acid addition and base salts thereof.

Suitable acid addition salts are formed from acids which form non-toxic salts. Examples include the acetate, aspartate, benzoate, besylate, bicarbonate, bisulphate, borate, bromide, camsylate, carbonate, chloride, citrate, edisylate, esylate, formate, fumarate, gluceptate, gluconate, glucuronate, hexafluorophosphate, hibenzate, hydrobromide, hydrochloride, hydroiodide, iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, sulphate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:

(i) by reacting the compound of formula (I) with the desired acid;

(ii) by removing an acid- or base-labile protecting group from a suitable precursor of the compound of formula (I) or by ring-opening a suitable cyclic precursor, for example, a lactone or lactam, using the desired acid; or (iii) by converting one salt of the compound of formula (I) to another by reaction with an appropriate acid or by means of a suitable ion exchange column.

All three reactions are typically carried out in solution. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

Complexes include clathrates, i.e. drug-host inclusion complexes wherein, in contrast to the aforementioned solvates, the drug and host are present in stoichiometric or non-stoichiometric amounts. Also included are complexes of the pharmaceutical drug which contain two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

The compounds of the present invention may have the ability to crystallize in more than one form, a characteristic known as polymorphism, and all such polymorphic forms ("polymorphs") are encompassed within the scope of the invention. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

Certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985).

As the compounds of formula (I) contain a secondary amino functionality (—NHR where R≠H), examples of prodrugs in accordance with the invention include amides thereof, produced, for example, by replacement of hydrogen with $(C_1-C_{10})$alkanoyl.

Further examples of replacement groups in accordance with the foregoing examples and examples of other prodrug types in accordance with the invention may be found in the aforementioned references.

Moreover, certain compounds of formula (I) may themselves act as prodrugs of other compounds of formula (I).

Also included within the scope of the invention are metabolites of compounds of formula (I), that is, compounds formed in vivo upon administration of the drug. Some examples of metabolites in accordance with the invention include:

(i) where the compound of formula (I) contains a methyl group, an hydroxymethyl derivative thereof (—$CH_3$->—$CH_2OH$);

(ii) where the compound of formula (I) contains a tertiary amino group, a secondary amino derivative thereof (—$NR^1R^2$->—$NHR^1$ or —$NHR^2$);

(iii) where the compound of formula (I) contains a secondary amino group, a primary derivative thereof (—NH-$R^1$->—$NH_2$);

(iv) where the compound of formula (I) contains a phenyl moiety, a phenol derivative thereof (-Ph->-PhOH); and (v) where the compound of formula (I) contains an amide group, a carboxylic acid derivative thereof (—CO-$NH_2$->COOH).

Compounds of formula (I) may contain one or more further asymmetric carbon atoms and therefore exist as two or more stereoisomers. Imidazole_substitution of the tropane ring in compounds of formula (I) can be in either endo- or exo-configuration, and therefore geometric cis/trans (or Z/E) isomers are possible. Where the compound contains, for example, a keto group, tautomeric isomerism ('tautomerism') may occur. It follows that a single compound may exhibit more than one type of isomerism.

Included within the scope of the present invention are all stereoisomers of the compounds of formula (I), including all optical isomers, geometric isomers and tautomeric forms as well as compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Imidazole substitution of the tropane ring in the endo-configuration is preferred.

Endo/exo isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E. L. Eliel (Wiley, New York, 1994).

The present invention also includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds of formula (I) can generally be prepared by conventional techniques known to those skilled in the art or by processes analogous to those described in the accompanying Examples and Preparations using an appropriate isotopically-labelled reagent in place of the non-labelled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Preferred compounds of formula (I) include the compounds of Examples 1-8; and pharmaceutically acceptable salts, solvates or derivatives thereof.

In the general processes, and schemes, that follow: $R^1$ and $R^2$ are as previously defined unless otherwise stated; Z is OH, or a carboxylic acid activating group such as chloro or 1H-imidazol-1-yl; EsGp is an ester-forming group, such as $C_{1-6}$ alkyl; Pg is an amino protecting group, such as boc; ArLg is a leaving group appropriate to aromatic nucleophilic substitution, such as those disclosed in Jerry March, Advanced Organic Chemistry (4th edition), Wiley Interscience, 1992, page 652 (incorporated herein by reference), e.g. F, Cl, Br, OMe or OEt; boc is t-butoxycarbonyl; DMF is N,N-dimethylformamide; DCM is dichloromethane; THF is tetrahydrofuran; Lg is a leaving group appropriate to aliphatic nucleophilic substitution, such as those disclosed in Jerry March, ibid, page 352 (incorporated herein by reference), including Cl, Br, I and sulfonic esters (e.g. tosylate, mesylate and triflate); WSCDI is 1-(3-dimethylaminopropyl)-3-ethylcarbodiimide hydrochloride; DCC is N,N'-dicyclohexylcarbodiimide; HOAT is 1-hydroxy-7-azabenzotriazole; HOBt is 1-hydroxybenzotriazole hydrate; HBTU is O-benzotriazol-1-yl-N,N,N',N'-tetramethyluronium hexafluorophosphate.

According to a first process (A) compounds of formula (I) may be prepared by reacting a compound of formula (II)

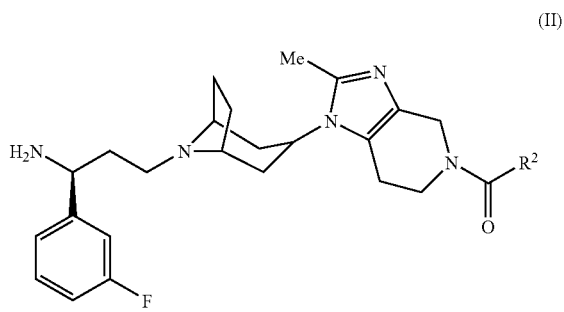

with a compound of formula (III)

under conventional carboxylic acid/amine coupling conditions. Conveniently, the coupling is effected under the conditions described hereinafter in connection with scheme 1, step (i).

According to a second process (B) compounds of formula (I) may be prepared by reacting a compound of formula (XVI)

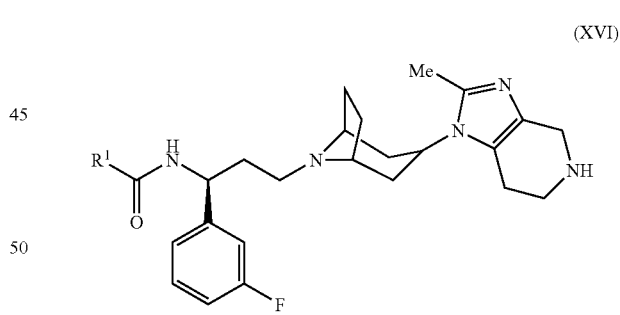

with a compound of formula (V)

under conventional carboxylic acid/amine coupling conditions. Conveniently, the coupling is effected under the conditions described hereinafter in connection with scheme 1a, step (i).

According to a third process (C) compounds of formula (I) may be prepared by reductive amination of an aldehyde of formula (XIX)

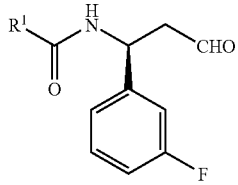

(XIX)

with an amine of formula (XX)

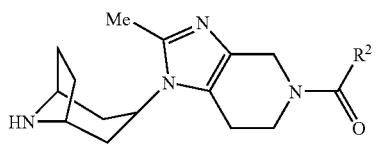

(XX)

under conventional conditions. Conveniently, reductive amination is effected under the conditions described hereinafter in connection with scheme 1, step (g).

According to a fourth process (D) compounds of formula (I) may be prepared by reductive amination of a nitrile of formula (XXI)

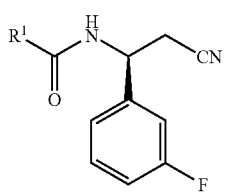

(XXI)

with an amine of formula (XX) under conventional conditions. Conveniently, reductive amination is effected under the conditions described hereinafter in connection with scheme 1, step (g).

According to a fifth process (E) compounds of formula (I) may be prepared by alkylation of an amine of formula (XX) with a compound of formula (XXII)

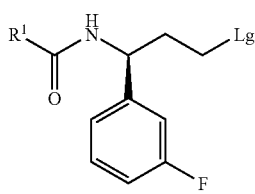

(XXII)

under conventional alkylation conditions. Conveniently, alkylation is effected in a suitable solvent, such as an haloalkane (e.g. DCM), an alcohol (e.g. ethanol) or an ether (e.g. THF); optionally in the presence of a base, such as an amine (e.g. triethylamine or N-ethyl-N,N-diisopropylamine); and at from ambient to elevated temperature (e.g. reflux).

According to another process (F) compounds of formula (I) may be prepared by asymmetric reduction of an enamide of formula (XXIII)

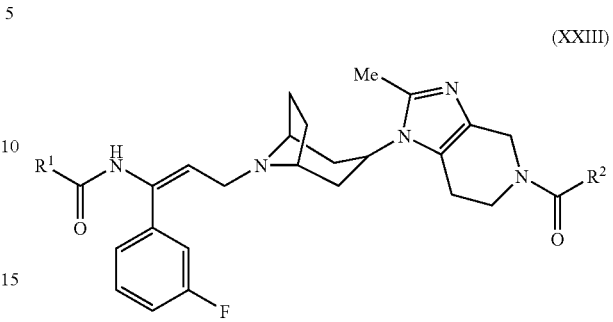

(XXIII)

under conventional reduction conditions. Conveniently, asymmetric reduction is effected in the presence of a transition metal such as Rh, Ru, Pd, Pt, Ir, or Ti (e.g. present in 0.001-0.1 mol eq.); a chiral ligand such as BINAP (2,2-bis(diphenylphosphino)-1,1'-binaphthyl), tol-BINAP (2,2-bis(di-p-tolylphosphino)-1,1'-binaphthyl), Du-PHOS (1,2-bis(2,5-dimethylphospholano)benzene) or Penn-Phos (P,P'-1,2-phenylenebis(endo-2,5-dimethyl-7-phosphabicyclo[2,2,1]heptane) (e.g. present in 0.001-0.2 mol eq.); a hydrogen donor such as molecular hydrogen, phenylsilane, 2-propanol or ammonium formate; in a solvent, such as an alcohol (e.g. methanol, ethanol or 2-propanol), a nitrile (e.g. acetonitrile), an ester (e.g. ethyl acetate), an ether (e.g. THF), or toluene; at from 0° C. to the reflux temperature; and optionally at an elevated pressure.

According to another process (G) compounds of formula (I) may be prepared from the amine of formula (II), or a metal salt thereof (i.e. a deprotonated form), by reaction with an ester of formula (XXIV)

$$R^1CO_2EsGp \qquad (XXIV)$$

under conventional conditions. Conveniently, the reaction is effected in the presence of an excess of a base, such as an amine (e.g. triethylamine or N-ethyl-N,N-diisopropylamine); an optional catalyst; in a suitable solvent, such as a haloalkane (e.g. DCM), an ether (e.g. THF), an ester (e.g. ethyl acetate), or toluene, with or without water present as a co-solvent. Alternatively, the reaction is effected in the presence of an enzyme-catalyst; in a suitable solvent such as a haloalkane (e.g. DCM), an ether (e.g. THF), an ester (e.g. ethyl acetate), or toluene, with or without water present as a co-solvent.

Schemes that further illustrate general methods for the preparation of compounds of formula (I), and intermediates thereto, follow.

It will be appreciated by those skilled in the art that certain of the procedures described in the schemes for the preparation of compounds of formula (I) or intermediates thereto may not be applicable to some of the possible substituents.

It will be further appreciated by those skilled in the art that it may be necessary or desirable to carry out the transformations described in the schemes in a different order from that described, or to modify one or more of the transformations, to provide the desired compound of formula (I).

It will be still further appreciated by those skilled in the art that, as illustrated in the schemes that follow, it may be necessary or desirable at any stage in the synthesis of compounds of formula (I) to protect one or more sensitive groups in the molecule so as to prevent undesirable side reactions. In particular, it may be necessary or desirable to protect amino groups. The protecting groups used in the preparation of compounds of formula (I) may be used in conventional manner. See, for example, those described in 'Protective Groups in Organic Synthesis' by Theodora W Green and Peter G M Wuts, third edition, (John Wiley and Sons, 1999), in particular chapter 7, pages 494-653 ("Protection for the Amino Group"), incorporated herein by reference, which also describes methods for the removal of such groups.

The amino protecting groups boc, benzyloxycarbonyl, methoxycarbonyl, benzyl and acetyl are of particular use in the preparation of compounds of formula (I) and intermediates thereto.

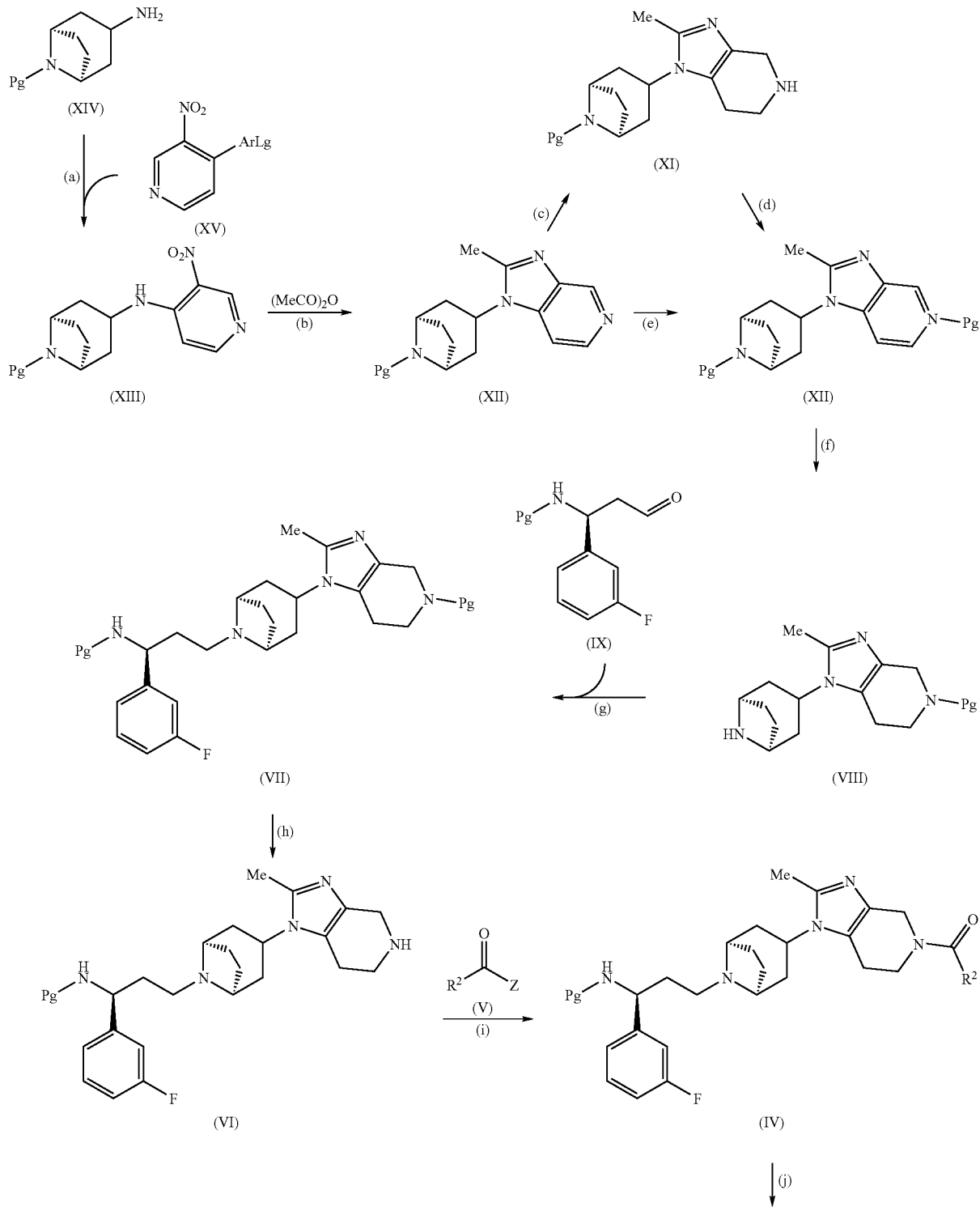

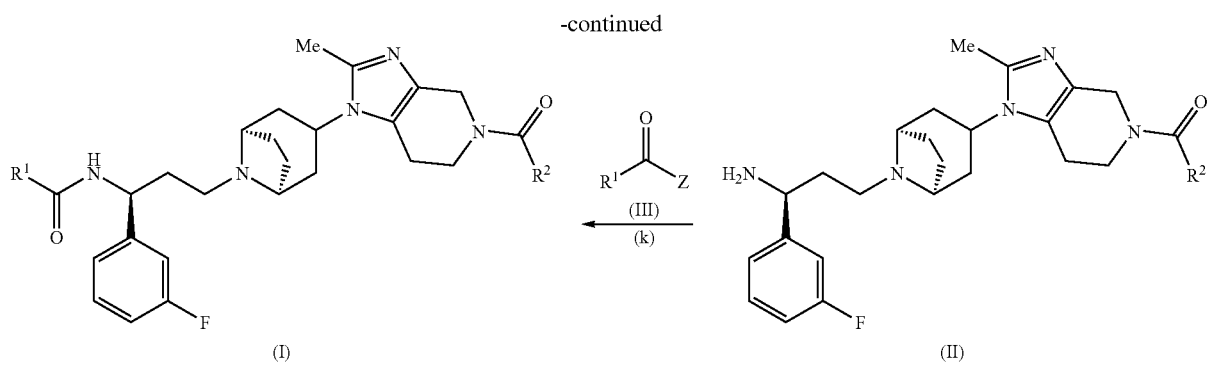

With specific reference to scheme 1, the transformations depicted therein may be effected as follows:

(a) Substitution of a leaving group on a nitropyridine of formula (XV) with an amine of formula (XIV) is conveniently effected in the presence of a base, such as an amine (e.g. triethylamine or N-ethyl-N,N-diisopropylamine) or an alkali metal carbonate (e.g. sodium carbonate or potassium carbonate); in a solvent, such as an alcohol (e.g. methanol or ethanol), a nitrile (e.g. acetonitrile) or an amide (e.g. DMF); and at from ambient to elevated temperature (e.g. up to about 120° C.).

(b) An imidazopyridine of formula (XII) may be prepared by reduction and in situ cyclisation of an amino-nitropyridine of formula (XIII). The reduction is conveniently effected in the presence of a reducing agent, such as iron powder; a solvent, such as a carboxylic acid (e.g. acetic acid); and at from ambient temperature up to about 120° C. Cyclisation of the intermediate amino-aminopyridine is conveniently effected by the addition of a acetic anhydride and at elevated temperature (e.g. about 140° C.).

(c) Reduction of an imidazopyridine of formula (XII) to an imidazopiperidine of formula (XI) is conveniently effected by catalytic hydrogenation in the presence of a suitable catalyst, such as a transition metal catalyst, for instance a platinum (e.g. platinum oxide) or a palladium (e.g. palladium hydroxide or palladium on carbon) catalyst; in a solvent, such as a an alcohol (e.g. methanol or ethanol) or a carboxylic acid (e.g. acetic acid); at ambient to elevated temperature (e.g. up to 80° C.; and at elevated pressure, such as from 150 to 500 kPa of hydrogen (e.g. 400 kPa hydrogen)

(d) The imidazopiperidine of formula (XI) may be protected by reaction with an alkyl chloroformate (e.g. methyl chloroformate). The reaction is conveniently carried out in a solvent, such as an haloalkane (e.g. DCM) or an ether (e.g. THF) using a base such as an amine (e.g. triethylamine or N-ethyl-N,N-diisopropylamine) at room temperature.

(e) In an alternative to steps (c) and (d), an imidazopyridine of formula (XII) is treated with a an alkyl chloroformate (e.g. methylchloroformate) and an amine base (e.g. triethylamine or N-ethyl-N,N-diisopropylamine), to give a quaternary intermediate, which is reduced under conventional conditions. Conveniently, methyl chloroformate is added to an imidazopyridine of formula (XII) in the presence of a solvent, such as an ether (e.g. THF) or a haloalkane (e.g. DCM) and at ambient temperature to give a quaternary intermediate, which is then reduced by the addition of an alkali metal halide, such as lithium borohydride, under conditions of reduced temperature (e.g. about −70° C.). The resulting intermediate is further reduced by catalytic hydrogenation in the presence of a suitable catalyst, such as a transition metal catalyst, for example a palladium (e.g. palladium hydroxide or palladium on carbon) catalyst; in a solvent, such as an alcohol (e.g. methanol or ethanol) or a carboxylic acid (e.g. acetic acid); at ambient to elevated temperature (e.g. up to 80° C.).

(f) Where the protecting group is an acetyl protecting group or like group, its removal is conveniently effected by treatment with a base, such as an alkali metal hydroxide (e.g. sodium or potassium hydroxide) or an acid, such as an inorganic acid (e.g. HCl) and at elevated temperature, such as from 60-100° C.

(g) Compounds of formula (VII) are prepared by reductive amination of an aldehyde of formula (IX) by an amine of formula (VIII). Conveniently, the reaction is carried out in the presence of an acid, such as an organic acid (e.g. acetic acid); in a solvent, such as an ether (e.g. THF) or a haloalkane (e.g. DCM); using an alkali metal hydride reducing agent, such as sodium triacetoxyborohydride, sodium cyanoborohydride or sodium borohydride; and at ambient temperature.

(h) Where protection under step (d) is afforded by means of a methoxycarbonyl group, its removal is conveniently effected by treatment with a base, such as an alkali metal hydroxide (e.g. sodium or potassium hydroxide) in a solvent, such as an aqueous alcohol (e.g. H$_2$O/propan-2-ol) at an elevated temperature (e.g. 100° C.).

(i) The acid/amine coupling is conveniently effected using an amine of formula (VI) and an acid chloride of formula (V); an excess of an acid acceptor, such as triethylamine or N-ethyl-N,N-diisopropylamine; a solvent, such as a haloalkane (e.g. DCM) or an ether (e.g. THF); and at ambient temperature.

Alternatively, the acid/amine coupling is effected using an acid of formula (V) activated by reagents such as WSCDI or DCC and HOBt or HOAt; an excess of an acid acceptor such as triethylamine or N-ethyl-N,N-diisopropylamine; a solvent, such as a haloalkane (e.g. DCM) or an ether (e.g. THF); and at ambient temperature.

(j) Where the protecting group is a boc protecting group, its removal is conveniently effected in the presence of an acid, such as an inorganic acid (e.g. anhydrous HCl) or trifluoroacetic acid; in a suitable solvent, such as an ester (e.g. ethyl acetate), haloalkane (e.g. DCM) or ether (e.g. THF); and from 0° C. to ambient temperature.

(k) The acid/amine is conveniently effected using an amine of formula (II) and an acid or acid chloride of formula (III), under the conditions described in step (i) hereinabove.

It will be appreciated by those skilled in the art that one or more of the transformations described in the scheme 1 may be carried out in a different order from that described, or may be modified, in order to provide the desired compound of formula (I).

In a variation of scheme 1, compounds of formula (I) may be prepared by carrying out steps (h) to (k) in a different order, as illustrated in scheme 1a that follows.

The compounds of formula (I) and their pharmaceutically acceptable salts, solvates and derivatives are useful because they have pharmacological activity in animals, including humans. More particularly, they are useful in the treatment of a disorder in which the modulation of CCR5 receptors is implicated. Disease states of particular interest include HIV, retroviral infections genetically related to HIV, AIDS, and inflammatory diseases.

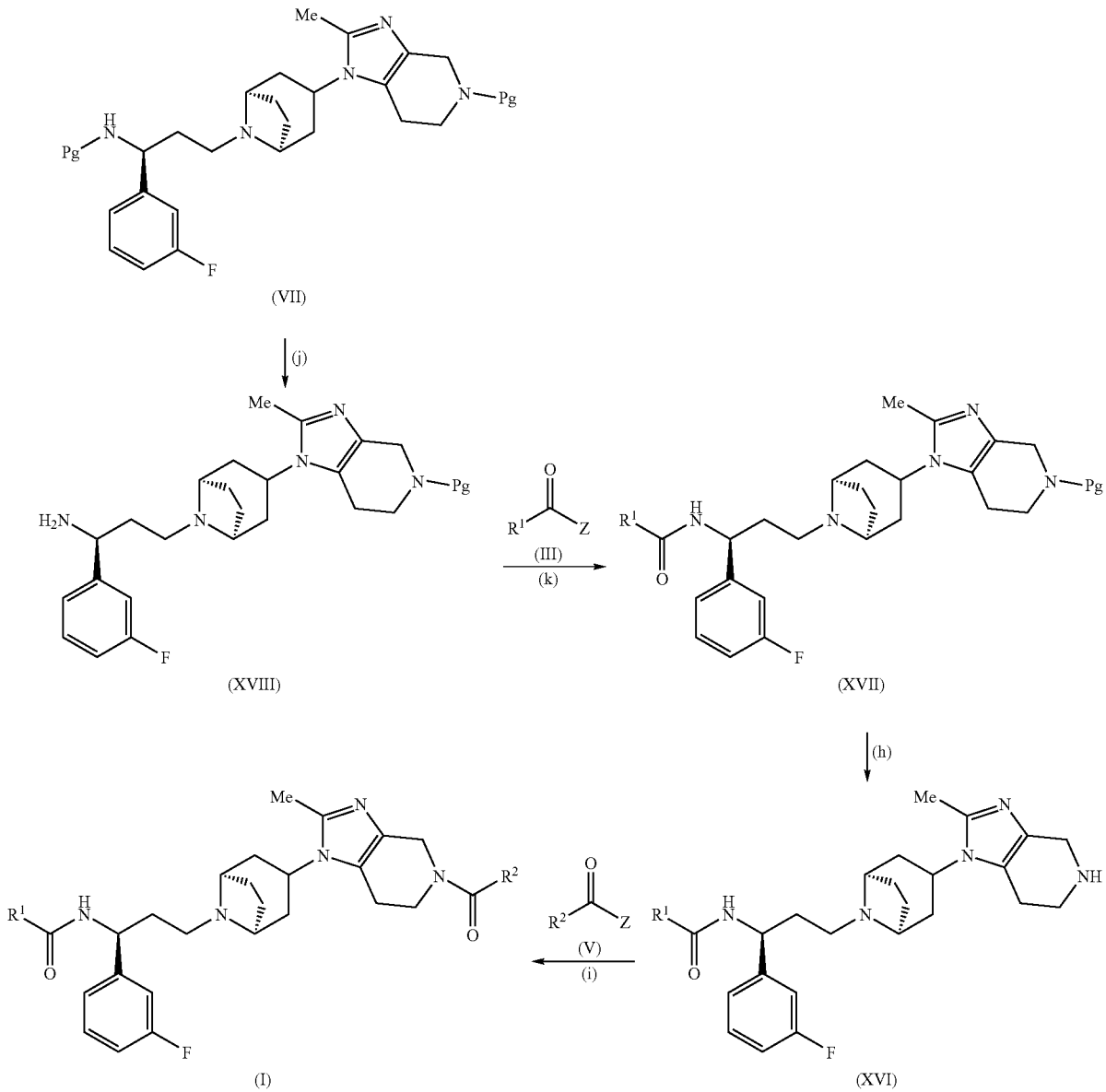

Scheme 1a

Compounds of formula (XX) are of analogous structure to compounds of formula (I), or intermediates thereto, and may be prepared by analogous methods.

Compounds of formulae (III), (V), (IX), (XV), (XIX), (XXI), (XXII) and (XXIII) are either known compounds or may be prepared by conventional chemistry; see, for example WO01/90106 (especially pages 5-19), incorporated herein by reference.

The compounds of this invention may be used for treatment of respiratory disorders, including adult respiratory distress syndrome (ARDS), bronchitis, chronic bronchitis, chronic obstructive pulmonary disease, cystic fibrosis, asthma, emphysema, rhinitis and chronic sinusitis.

Other conditions that may be treated are those triggered, affected or are in any other way correlated with T-cell trafficking in different organs. It is expected that the compounds of this invention may be useful for the treatment of such conditions and in particular, but not limited to, conditions for which a correlation with CCR5 or CCR5 chemokines has been established, and more particularly, but not limited to, the following: multiple sclerosis; arthritis, such as rheumatoid arthritis, spondyloarthropathies, gouty arthritis, osteoarthritis, systemic lupus erythematosus and juvenile arthritis; and graft rejection, in particular, but not limited to, solid organ transplants, such as heart, lung, liver, kidney and pancreas transplants (e.g. kidney and lung allografts). Other conditions for which a similar correlation with CCR5 or CCR5 chemokines has been established include, but are not limited to: inflammatory bowel disease, including Crohn's disease and ulcerative colitis; endometriosis; type I diabetes; renal diseases, such as glomerular disease (e.g. glomerulonephritis); fibrosis, such as liver, pulmonary and renal fibrosis; chronic pancreatitis; inflammatory lung conditions; encephalitis, such as HIV encephalitis; chronic heart failure; ischaemic heart disease; psoriasis; stroke; obesity; CNS diseases, such as AIDS related dementias and Alzheimer's Disease; anaemia; restenosis; atherosclerotic plaque; atopic dermatitis; chronic pancreatitis; cancer, such as non-Hodgkin's lymphoma, Kaposi's sarcoma, melanoma and breast cancer; pain, such as nociceptive pain and neuropathic pain (e.g. peripheral neuropathic pain); and stress response resulting from surgery, infection, injury or other traumatic insult.

Infectious diseases where modulation of the CCR5 receptor is implicated include acute and chronic hepatitis B Virus (HBV) and hepatitis C Virus (HCV) infection; bubonic, septicemic, and pneumonic plague; pox virus infection, such as smallpox; toxoplasmosis infection; mycobacterium infection; trypanosomal infection such as Chagas' Disease; pneumonia; and cytosporidiosis.

For a recent review of possible applications of chemokines and chemokine receptor blockers see Cascieri, M. A., and Springer, M. S., "The chemokine/chemokine receptor family: potential and progress for therapeutic intervention", Curr. Opin. Chem. Biol., 4(4), 420-7 (August 2000).

Accordingly, in another aspect the invention provides a compound of formula (I) or a pharmaceutically acceptable salt, solvate or derivative thereof for use as a medicament.

In another aspect the invention provides a compound of formula (I) or a pharmaceutically acceptable salt, solvate or derivative thereof, for the treatment of a disorder in which the modulation of CCR5 receptors is implicated.

In another aspect the invention provides a compound of formula (I) or a pharmaceutically acceptable salt, solvate or derivative thereof, for the treatment of HIV, a retroviral infection genetically related to HIV, AIDS, or an inflammatory disease.

In another aspect the invention provides a compound of formula (I) or a pharmaceutically acceptable salt, solvate or derivative thereof, for the treatment of a respiratory disorder including adult respiratory distress syndrome (ARDS), bronchitis, chronic bronchitis, chronic obstructive pulmonary disease, cystic fibrosis, asthma, emphysema, rhinitis or chronic sinusitis.

In another aspect the invention provides a compound of formula (I) or a pharmaceutically acceptable salt, solvate or derivative thereof, for the treatment of multiple sclerosis, rheumatoid arthritis or graft rejection.

In another aspect the invention provides a compound of formula (I) or a pharmaceutically acceptable salt, solvate or derivative thereof, for the treatment of inflammatory bowel disease; endometriosis; type I diabetes; renal diseases; fibrosis; chronic pancreatitis; inflammatory lung conditions; encephalitis; chronic heart failure; ischaemic heart disease; psoriasis; stroke; obesity; CNS diseases; anaemia; restenosis; atherosclerotic plaque; atopic dermatitis; chronic pancreatitis; cancer; pain; or stress response resulting from surgery, infection, injury or other traumatic insult.

In another aspect the invention provides a compound of formula (I) or a pharmaceutically acceptable salt, solvate or derivative thereof, for the treatment of HBV, HCV, plague, pox virus, toxoplasmosis, mycobacterium, trypanosomal, pneumonia, or cytosporidiosis.

In another aspect the invention provides the use of a compound of formula (I) or of a pharmaceutically acceptable salt, solvate or derivative thereof, for the manufacture of a medicament for the treatment of a disorder in which the modulation of CCR5 receptors is implicated.

In another aspect the invention provides a method of treatment of a mammalian disorder in which the modulation of CCR5 receptors is implicated which comprises treating said mammal with an effective amount of a compound of formula (I) or with a pharmaceutically acceptable salt, solvate or derivative thereof.

The compounds of the invention may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or in any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the invention and methods for their preparation will be readily apparent to those skilled in the art. Such compositions and methods for their preparation may be found, for example, in 'Remington's Pharmaceutical Sciences', 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 0.1 wt % to 80 wt %, more typically from 1 wt % to 60 wt %, such as 5 wt % to 50 wt %, of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 0.1 wt % to 25 wt %, more typically from 0.5 wt % to 20 wt %, such as 1 wt % to 15 wt %, of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch, calcium carbonate and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colourants, flavours, preservatives and taste-masking agents.

Exemplary tablets contain up to about 80% drug, from about 10 wt % to about 90 wt % binder, from about 0 wt % to about 85 wt % diluent, from about 1 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the compound. Examples of such formulations include drug-coated stents and PGLA microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound comprising, for example, ethanol (optionally, aqueous ethanol) or a suitable alternative agent for dispersing, solubilising, or extending release of the compound, the propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insulator may be formulated to contain a powder mix of the compound of the invention, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μg to 100 μl. A typical formulation may comprise a compound of the invention, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid) (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 μg to 10 mg of the compound of the invention. The overall daily dose will typically be in the range 1 μg to 200 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a compound of the invention in combination with another therapeutic agent, for example, for the purpose of treating a particular disease or condition, it is within the scope of the present invention that two or more pharmaceutical compositions, at least one of which contains a compound of the invention, may conveniently be combined in the form of a kit suitable for coadministration of the compositions.

Thus the kit of the invention comprises two or more separate pharmaceutical compositions, at least one of which contains a compound of formula (I) or a pharmaceutically acceptable salt, solvate or derivative thereof, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, having a weight of about 65 to 70 kg, the total daily dose of a compound of the invention is typically in the range 1 to 10,000 mg, such as 10 to 1,000 mg, for example 25 to 500 mg, depending, of course, on the mode of administration, the age, condition and weight of the patient, and will in any case be at the ultimate discretion of the physician. The total daily dose may be administered in single or divided doses.

Accordingly in another aspect the invention provides a pharmaceutical composition including a compound of formula (I) or a pharmaceutically acceptable salt, solvate or derivative thereof together with one or more pharmaceutically acceptable excipients, diluents or carriers.

The compounds of formula (I) and their pharmaceutically acceptable salts, solvates and derivatives have the advantage that they are more selective, have a more rapid onset of action, are more potent, are better absorbed, are more stable, are more resistant to metabolism, have a reduced 'food effect', have an improved safety profile or have other more desirable properties (e.g. with respect to solubility or hygroscopicity) than the compounds of the prior art.

In particular, the compounds of the invention have reduced inhibitory activity at the HERG potassium channel. Prolongation of the cardiac action potential duration (QT prolongation) has been identified as being due to action at the HERG potassium channel (Expert Opinion of Pharmacotherapy, 2, pp 947-973, 2000). QT prolongation is known to have a potential liability to produce fatal cardiac arrhythmias of Torsades de Pointes (TdP). In providing compounds which exhibit further reduced inhibitory activity at the HERG potassium channel with comparable or improved pharmacokinetics, the invention provides compounds which are therapeutically effective CCR5 antagonists with further improved cardiac safety.

The compounds of formula (I) and their pharmaceutically acceptable salts, solvates and derivatives may be administered alone or as part of a combination therapy. Thus included within the scope of the present invention are embodiments comprising coadministration of, and compositions which contain, in addition to a compound of the invention, one or more additional therapeutic agents. Such multiple drug regimens, often referred to as combination therapy, may be used in the treatment and prevention of any of the diseases or conditions mediated by or associated with CCR5 chemokine receptor modulation, particularly infection by human immunodeficiency virus, HIV. The use of such combination therapy is especially pertinent with respect to the treatment and prevention of infection and multiplication of the human immunodeficiency virus, HIV, and related pathogenic retroviruses within a patient in need of treatment or one at risk of becoming such a patient. The ability of such retroviral pathogens to evolve within a relatively short period of time into strains resistant to any monotherapy which has been administered to said patient is well known in the literature. A recommended treatment for HIV is a combination drug treatment called Highly Active Anti-Retroviral Therapy, or HAART. HAART combines three or more HIV drugs. Thus, the methods of treatment and pharmaceutical compositions of the present invention may employ a compound of the invention in the form of monotherapy, but said methods and compositions may also be used in the form of combination therapy in which one or more compounds of the invention are coadministered in combination with one or more additional therapeutic agents such as those described in detail further herein.

In a further embodiment of the invention, combinations of the present invention include treatment with a compound of formula (I), or a pharmaceutically acceptable salt, solvate or derivative thereof, and one or more additional therapeutic agents selected from the following: HIV protease inhibitors (PIs), including but not limited to indinavir, ritonavir, saquinavir, nelfinavir, lopinavir, amprenavir, atazanavir, tipranavir, AG1859 and TMC 114; non-nucleoside reverse transcriptase inhibitors (NNRTIs), including but not limited to: nevirapine; delavirdine; capravirine; efavirenz; 5-{[3,5-Diethyl-1-(2-hydroxyethyl)-1H-pyrazol-4-yl]oxy}isophthalonitrile or pharmaceutically acceptable salts, solvates or derivatives thereof; 5-{[3-Cyclopropyl-1-(2-hydroxyethyl)-5-methyl-1H-pyrazol-4-yl]oxy}isophthalonitrile or pharmaceutically acceptable salts, solvates or derivatives thereof; GW-8248; GW-5634 and TMC125; nucleoside/nucleotide reverse transcriptase inhibitors (NRTIs), including but not limited to zidovudine, didanosine, zalcitabine, stavudine, lamivudine, abacavir, adefovir dipivoxil, tenofovir, emtricitabine and alovudine; other CCR5 antagonists, including but not limited to:

N-{(1S)-3-[3-(3-isopropyl-5-methyl-4H-1,2,4-triazol-4-yl)-exo-8-azabicyclo[3.2.1]oct-8-yl]-1-phenylpropyl}-4,4-difluorocyclohexanecarboxamide or pharmaceutically acceptable salts, solvates or derivatives thereof, methyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate or pharmaceutically acceptable salts, solvates or derivatives thereof, methyl 3-endo-{8-[(3S)-3-(acetamido)-3-(3-fluorophenyl)propyl]-8-azabicyclo[3.2.1]oct-3-yl}-2-methyl-4,5,6,7-tetrahydro-3H-imidazo[4,5-c]pyridine-5-carboxylate or pharmaceutically acceptable salts, solvates or derivatives thereof, ethyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate or pharmaceutically acceptable salts, solvates or derivatives thereof, Sch D, ONO4128, GW873140, AMD-887 and CMPD-167; agents which inhibit the interaction of gp120 with CD4, including but not limited to BMS806, BMS-488043, 5-{(1S)-2-[(2R)-4-Benzoyl-2-methyl-piperazin-1-yl]-1-methyl-2-oxo-ethoxy}-4-methoxy-pyridine-2-carboxylic acid methylamide and 4-{(1S)-2-[(2R)-4-Benzoyl-2-methyl-piperazin-1-yl]-1-methyl-2-oxo-ethoxy}-3-methoxy-N-methyl-benzamide; other agents which inhibit the entry of HIV into a target cell, including but not limited to enfuviritide, T1249, PRO542 and PRO140; integrase inhibitors, including but not limited to L-870,810; and RNaseH inhibitors.

There is also included within the scope the present invention, combinations of a compound of formula (I), or a pharmaceutically acceptable salt, solvate or derivative thereof, together with one or more additional therapeutic agents independently selected from the group consisting of proliferation inhibitors, e.g. hydroxyurea; immunomodulators, such as granulocyte macrophage colony stimulating growth factors (e.g. sargramostim), tachykinin receptor modulators (e.g. NK1 antagonists) and various forms of interferon or interferon derivatives; other chemokine receptor agonists/antagonists such as CXCR4 antagonists (e.g AMD-070); agents which substantially inhibit, disrupt or decrease viral transcription or RNA replication such as inhibitors of tat (transcriptional trans activator) or nef (negative regulatory factor); agents which substantially inhibit, disrupt or decrease translation of one or more proteins expressed by the virus (including, but not limited to, down regulation of protein expression or antagonism of one or more proteins) other than reverse transcriptase, such as Tat or Nef; agents which influence, in particular down regulate, CCR5 receptor expression; chemokines that induce CCR5 receptor internalisation such MIP-1α, MIP-1β, RANTES and derivatives thereof; and other agents that inhibit viral infection or improve the condition or outcome of HIV-infected individuals through different mechanisms.

Agents which influence (in particular down regulate) CCR5 receptor expression include immunosupressants, such as calcineurin inhibitors (e.g. tacrolimus and cyclosporin A); steroids; agents which interfere with cytokine production or signalling, such as Janus Kinase (JAK) inhibitors (e.g. JAK-3 inhibitors, including 3-{(3R,4R)-4-methyl-3-[methyl-(7H-pyrrolo[2,3-d]pyrimidin-4-yl)-amino]-piperidin-1-yl}-3-oxo-propionitrile) and pharmaceutically acceptable salts, solvates or derivatives thereof; cytokine antibodies (e.g. antibodies that inhibit the interleukin-2 (IL-2) receptor, including basiliximab and daclizumab); and agents which interfere with cell activation or cell cycling, such as rapamycin.

There is also included within the scope the present invention, combinations of a compound of formula (I), or a pharmaceutically acceptable salt, solvate or derivative thereof, together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include, but are not limited to, ritonavir, saquinavir or ketoconazole.

It will be appreciated by a person skilled in the art, that a combination drug treatment, as described herein above, may comprise two or more compounds having the same, or different, mechanism of action. Thus, by way of illustration only, a combination may comprise a compound of the invention and: one or more NRTIs; one or more NRTIs and a PI; one or more NRTIs and another CCR5 antagonist; a PI; a PI and an NNRTI; an NNRTI; and so on.

In addition to the requirement of therapeutic efficacy, which may necessitate the use of therapeutic agents in addition to the compounds of the invention, there may be additional rationales which compel or highly recommend the use of a combination of a compound of the invention and another therapeutic agent, such as in the treatment of diseases or conditions which directly result from or indirectly accompany the basic or underlying CCR5 chemokine receptor modulated disease or condition. For example, where the basic CCR5 chemokine receptor modulated disease or condition is HIV infection and multiplication it may be necessary or at least desirable to treat Hepatitis C Virus (HCV), Hepatitis B Virus (HBV), Human Papillomavirus (HPV), opportunistic infections (including bacterial and fungal infections), neoplasms, and other conditions which occur as the result of the immune-compromised state of the patient being treated. Other therapeutic agents may be used with the compounds of the invention, e.g., in order to provide immune stimulation or to treat pain and inflammation which accompany the initial and fundamental HIV infection.

Accordingly, therapeutic agents for use in combination with the compounds of formula (I) and their pharmaceutically acceptable salts, solvates and derivatives also include: interferons, pegylated interferons (e.g. peginterferon alfa-2a and peginterferon alfa-2b), lamivudine, ribavirin and emtricitabine for the treatment of hepatitis; antifungals such as fluconazole, fosfluconazole, itraconazole, and voriconazole; antibacterials such as azithromycin and clarithromycin; interferons, daunorubicin, doxorubicin, and paclitaxel for the treatment of AIDS related Kaposi's sarcoma; and cidofovir, fomivirsen, foscarnet, ganciclovir and valcyte for the treatment of cytomegalovirus (CMV) retinitis.

Further combinations for use according to the invention include combination of a compound of formula (I), or a pharmaceutically acceptable salt, solvate or derivative thereof with a CCR1 antagonist, such as BX-471; a beta adrenoceptor agonist, such as salmeterol; a corticosteroid agonist, such fluticasone propionate; a LTD4 antagonist, such as montelukast; a muscarinic antagonist, such as tiotropium bromide; a PDE4 inhibitor, such as cilomilast or roflumilast; a COX-2 inhibitor, such as celecoxib, valdecoxib or rofecoxib; an alpha-2-delta ligand, such as gabapentin or pregabalin; a beta-interferon, such as REBIF; a TNF receptor modulator, such as a TNF-alpha inhibitor (e.g. adalimumab), a HMG CoA reductase inhibitor, such as a statin (e.g. atorvastatin); or an immunosuppressant, such as cyclosporin or a macrolide such as tacrolimus.

In the above-described combinations, the compound of formula (I) or a pharmaceutically acceptable salt, solvate or derivative thereof and other therapeutic agent(s) may be administered, in terms of dosage forms, either separately or in conjunction with each other; and in terms of their time of administration, either simultaneously or sequentially. Thus, the administration of one component agent may be prior to, concurrent with, or subsequent to the administration of the other component agent(s).

Accordingly, in a further aspect the invention provides a pharmaceutical composition comprising a compound of formula (I) or a pharmaceutically acceptable salt, solvate or derivative thereof and one or more additional therapeutic agents.

It is to be appreciated that all references herein to treatment include curative, palliative and prophylactic treatment.

EXAMPLES

The invention is illustrated by the following Examples and Preparations in which the following further abbreviations may be used:

h=hour min=minute

LRMS=low resolution mass spectrum

HRMS=high resolution mass spectrum

APCI+=atmospheric pressure chemical ionisation

ESI+=electrospray ionisation

NMR=nuclear magnetic resonance tlc—thin layer chromatography

Me=methyl

Example 1

N-{(1S)-3-[3-endo-(5-Acetyl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide

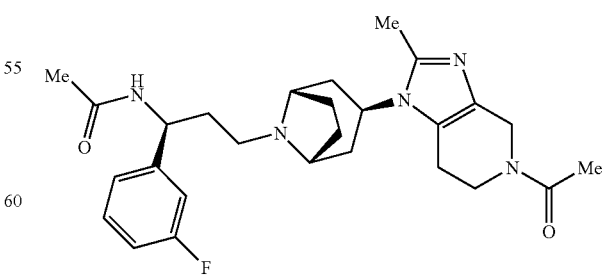

To a stirred solution of the amine N-{(1S)-3-[3-endo-(2-Methyl-4,5,6,7-tetrahydro-1H-imidazo[4,5-c]pyridin-1-yl)-8-azabicyclo[3.2.1]oct-8-yl]-1-(3-fluorophenyl)propyl} acetamide (94 mg, 0.21 mmol) in dichloromethane (5 ml), at room temperature, was added acetyl chloride (18 μl, 0.26 mmol) followed by N,N-diiso-propylethylamine (45 μl, 0.26 mmol). After 15 hours the reaction mixture was diluted with dichloromethane (5 ml) and water (5 ml) and then passed through a phase separation cartridge. The organic component was concentrated by passing a stream of nitrogen over the solution and the resulting mixture was purified using a Mega Bond Elut$^{Flash}$ Si cartridge (10 g, Varian) eluting with dichloromethane:methanol:concentrated aqueous ammonia (95:5: 0.5, by volume) to give the title compound as a white foam (80 mg, 79%).

LRMS (electrospray): m/z [M+Na$^+$] 504, [MH$^+$] 482

Found C, 63.35; H, 7.32; N, 13.59. $C_{27}H_{36}N_5FO_2$. 0.5 $CH_2Cl_2$ requires C, 63.03; H, 7.12; N, 13.36.

[α]$_D$ −21.7° (2.12 mg/ml in MeOH)

Examples 2-3

These Examples were prepared according to the method described above for Example 1 using N-{(1S)-3-[3-endo-(2-Methyl-4,5,6,7-tetrahydro-1H-imidazo[4,5-c]pyridin-1-yl)-8-azabicyclo[3.2.1]oct-8-yl]-1-(3-fluorophenyl)propyl}acetamide and the corresponding compound of formula (V). All LRMS was electrospray ionisation.

Example 2

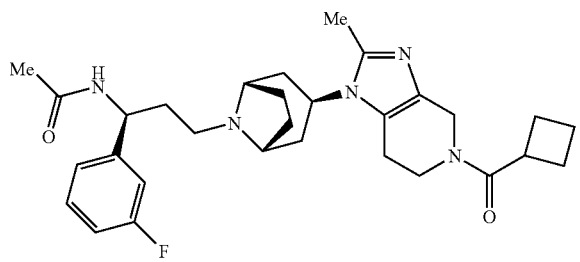

LRMS: m/z [MH$^+$] 522

Found C, 67.01; H, 7.74; N, 12.94. $C_{30}H_{40}FN_5O_2$. 0.1H$_2$O requires C, 66.77; H, 7.84; N, 12.93%.

[α]$_D$ −20.9° (2.04 mg/ml in MeOH)

Example 3

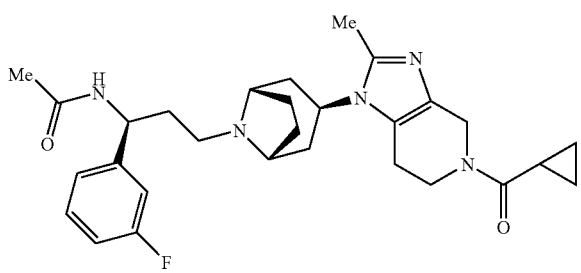

LRMS: m/z [MH$^+$] 508

Found C, 66.53; H, 7.59; N, 13.23. $C_{29}H_{38}FN_5O_2$. 0.1H$_2$O requires C, 66.26; H, 7.67; N, 13.32%.

[α]$_D$ −20.5° (2.38 mg/ml in MeOH)

Example 4

N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide

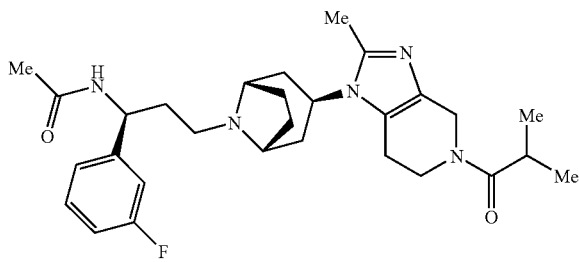

To a stirred solution of amine N-{(1S)-3-[3-endo-(2-Methyl-4,5,6,7-tetrahydro-1H-imidazo[4,5-c]pyridin-1-yl)-8-azabicyclo[3.2.1]oct-8-yl]-1-(3-fluorophenyl)propyl}acetamide (19.9 g, 45.3 mmol) in tetrahydrofuran (500 ml) was added triethylamine (7.0 ml, 50.0 mmol), followed by dropwise addition of isobutyryl chloride (5.3 ml, 50.mmol). After 1 hour a second portion of isobutyryl chloride was added dropwise (0.5 ml, 5.0 mmol). After 0.5 hour the reaction mixture was concentrated to approximately 300 ml and ethylacetate (200 ml) was added. The reaction mixture was washed with 10% aq. K$_2$CO$_3$ solution (200 ml; w/v). The aqueous phase was separated and extracted with ethylacetate (100 ml). The organic components were combined, washed with brine (100 ml), dried (MgSO$_4$) and concentrated until a mobile oil was obtained which had just started to form a foam. The residue was dissolved in ethyl acetate (100 ml) and heated to 90° C. Water (0.5 ml) was added to the hot solution and the mixture was allowed to slowly cool to room temperature. The precipitate was collected by filtration, washed with ethyl acetate (50 ml) and dried under reduced pressure to give the title compound as a white solid (20.9 g, 90%).

LRMS: m/z [MH$^+$] 510

$^1$H NMR (400 MHz, CD$_3$OD): δ: 7.29-7.35 (1H, m), 7.12-7.14 (1H, m), 7.05-7.07 (1H, m), 6.92-6.97 (1H, m), 5.13-5.17 (1H, m), 4.52-4.63 (1H, m), 4.43-4.44 (2H, m), 3.78-3.89 (2H, m), 3.31-3.40 (2H, m), 2.90-3.06 (1H, m), 2.77-2.84 and 2.69-2.75 (2H, 2×m), 2.39-2.51 (2H, m), 2.36 and 2.35 (3H, 2×s), 2.20-2.30 (2H, m), 2.03-2.13 (2H, m), 1.95 (3H, s), 1.84-1.90 (2H, m), 1.55-1.65 (4H, m), 1.08-1.11 and 1.04-1.06 (6H, 2×m). Rotamers.

Found C, 66.94; H, 7.92; N, 13.47. $C_{29}H_{40}FN_5O_2$.0.5H$_2$O. requires C, 67.16; H, 7.97; N, 13.50.

[α]$_D$ −23.4° (1.64 mg/ml in MeOH)

Examples 5-7

These Examples were prepared according to method described above for Example 1 using N-{(1S)-3-[3-endo-(2-Methyl-4,5,6,7-tetrahydro-1H-imidazo[4,5-c]pyridin-1-yl)-8-azabicyclo[3.2.1]oct-8-yl]-1-(3-fluorophenyl)propyl}acetamide and the corresponding compound of formula (V). All LRMS was electrospray, except for Ex 6, which was atmospheric pressure chemical ionisation.

Example 5

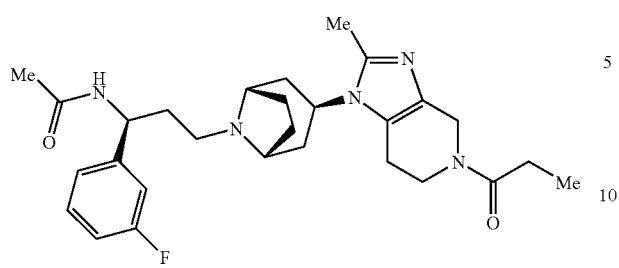

LRMS: m/z 496 [MH⁺]
Found C, 67.47; H, 7.75; N, 14.06. $C_{28}H_{38}FN_5O_2 \cdot 0.15H_2O$ requires C, 67.49; H, 7.75; N, 14.05%.
$[\alpha]_D$ −21.5° (2.00 mg/ml in MeOH)
(NMR data follow at the table end)

Example 6

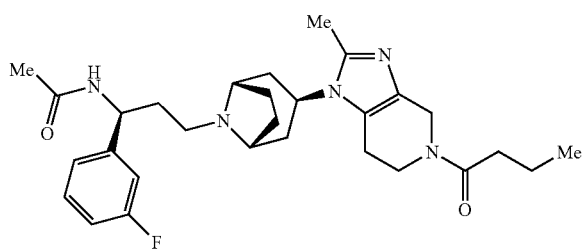

LRMS 532 [M+Na⁺], 510 [MH⁺]
Found C, 65.69; H, 7.97; N, 13.06. $C_{29}H_{40}FN_5O_2 \cdot 0.1H_2O$ requires C, 66.01; H, 8.02; N, 13.27%.
$[\alpha]_D$ −25.5° (2.14 mg/ml in MeOH)

Example 7

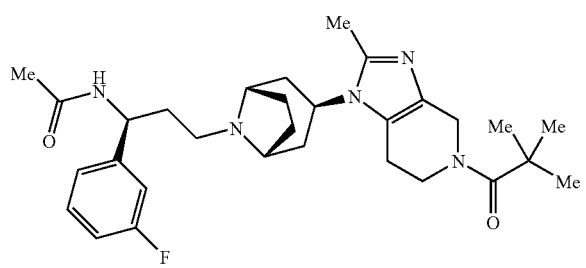

LRMS (electrospray) 546 [M+Na⁺], 524 [MH⁺]
Found C, 65.50; H, 7.93; N, 12.45. $C_{30}H_{42}FN_5O_2 \cdot 0.15H_2O$ requires C, 65.43; H, 8.24; N, 12.72%.
$[\alpha]_D$ −28.2° (2.06 mg/ml in MeOH)

Example 5 NMR

N-{(1S)-3-[3-endo-(2-Methyl-5-propionyl-4,5,6,7-tetrahydro-1H-imidazo[4,5-c]pyridin-1-yl)-8-azabicyclo[3.2.1]oct-8-yl]-1-(3-fluorophenyl)propyl}acetamide ¹H NMR (400 MHz, CD₃OD): δ: 7.31-7.37 (1H, m), 7.14-7.16 (1H, d), 7.06-7.10 (1H, m), 6.94-6.99 (1H, m), 5.14-5.21 (1H, m), 4.56-4.63 (1H, m), 4.40 and 4.45 (2H, 2×s), 3.81-3.89 (1H, m), 3.75-3.80 (1H, m), 3.33-3.41 (2H, m), 2.78-2.86 (1H, m), 2.70-2.76 (1H, m), 2.40-2.54 (4H, m), 2.37 and 2.38 (3H, 2×s), 2.23-2.30 (2H, m), 2.07-2.14 (2H, m), 1.98 (3H, s), 1.86-1.93 (2H, m), 1.57-1.67 (4H, m), 1.07-1.17 (3H, m). Rotamers.

Example 8

N-{(1S)-3-[3-endo-(2-Methyl-5-(3,3,3-trifluoropropionyl)-4,5,6,7-tetrahydro-1H-imidazo[4,5-c]pyridin-1-yl)-8-azabicyclo[3.2.1]oct-8-yl]-1-(3-fluorophenyl)propyl}acetamide

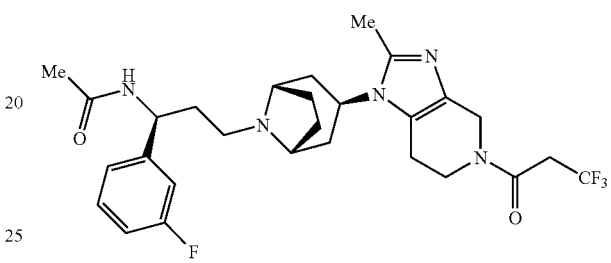

To a stirred solution of 3,3,3-trifluoropropionic acid (15 μl, 1.71 mmol) in dichloromethane (2 ml) was added O-benzotriazol-1-yl-N,N,N',N'-tetramethyluronium hexafluorophosphate (65 mg, 1.71 mmol), triethylamine (47 μl, 3.41 mmol) followed by the amine N-{(1S)-3-[3-endo-(2-Methyl-4,5,6,7-tetrahydro-1H-imidazo[4,5-c]pyridin-1-yl)-8-azabicyclo[3.2.1]oct-8-yl]-1-(3-fluorophenyl)propyl}acetamide (50 mg, 1.14 mmol). The reaction mixture was heated at 30° C. for 15 hours, concentrated by passing a stream of nitrogen over the solution, and purified by preparative HPLC (Phenomenex C₁₈ 15×10 cm 10 μm column, 20 ml/min flow rate, 225 nm detection, mobile phase gradient 95:5 to 5:95 A:B, (A: 0.1% diethylamine in H₂O, B: MeCN)) to give the title compound as a gum (20 mg).

LRMS (electrospray) 550 [MH⁺]
HRMS (electrospray). Found 550.2800. $C_{28}H_{36}N_5F_4O_2$ (MH⁺), requires 550.2800.

Example 9

N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide fumarate

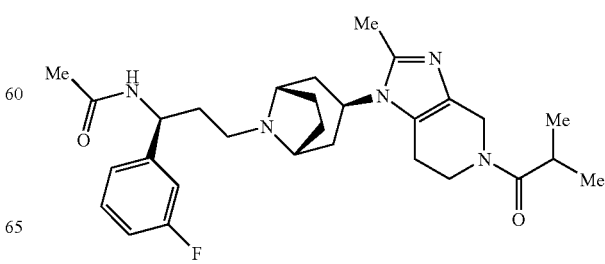

-continued

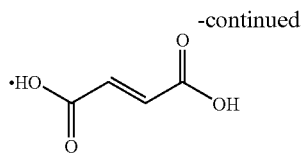

To a solution of N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide (300 mg, 0.59 mmol) in tetrahydrofuran (2 ml) at reflux was added a solution of fumaric acid (68 mg, 0.59 mmol) in hot ethanol (2 ml) dropwise. After 48 hours tetrahydrofuran (2 ml) was added and after a 48 hours the crystals were collected by filtration, washed with tetrahydrofuran (2 ml) and air dried to give the title compound as a white powder (110 mg, 30%).

Found C, 62.04; H, 7.26; N, 10.70. $C_{33}H_{44}FN_5O_6 \cdot 0.75H_2O$ requires C, 62.00; H, 7.17; N, 10.96.

Example 10

N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide

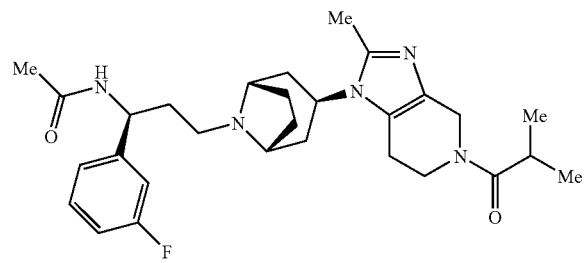

N-{(1S)-3-[3-endo-(2-Methyl-4,5,6,7-tetrahydro-1H-imidazo[4,5-c]pyridin-1-yl)-8-azabicyclo[3.2.1]oct-8-yl]-1-(3-fluorophenyl)propyl}acetamide (264.4 g, 0.60 mol) was added to propan-2-ol (2.67 L), followed by potassium carbonate (92.7 g, 0.67 mol) and the result was cooled to 15° C. iso-Butyryl chloride (97.8 g, 0.91 mol) was then added over 10 minutes, maintaining a temperature below 25° C. and after stirring for 10 minutes the reaction was complete. Potassium carbonate (267.2 g) in water (2.40 L) was then added and the resulting 2 phases separated. The aqueous layer was then extracted with ethyl acetate (2.67 L) and the combined organics were washed with saturated aqueous sodium chloride (1.32 L) and water (800 mL), then concentrated under vacuum. The residue was diluted with ethyl acetate (1.07 L) and concentrated again under vacuum. This redilution and concentration step was repeated and the resulting residue was treated with ethyl acetate until a total volume of 1.07 L had been reached. This was cooled to 0-5° C., stirred for 2 hours, filtered and washed with cold ethyl acetate (2×130 mL). The solid product was then dried in a vacuum oven at 50° C. to give the title compound (269.8 g, 0.53 mol, 88.0%).

Example 11

N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide fumarate

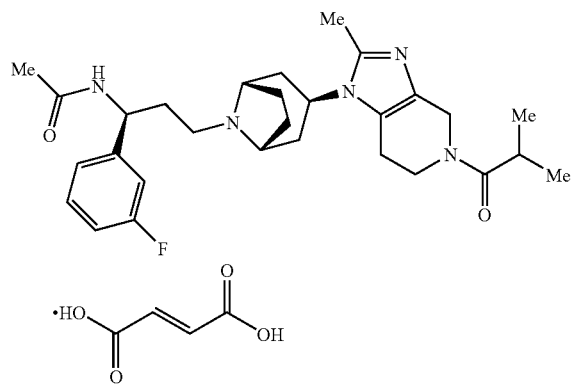

N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide (554.0 g, 1.08 mol) was added to propan-2-ol (13.85 L), followed by fumaric acid (126.2 g, 1.09 mol) and the result was warmed to reflux and stirred for 20 minutes. This solution was then clarified by filtration at this temperature, before being concentrated under vacuum to a solvent volume of 4 mL/g based on starting N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide. This was cooled to 0-5° C., stirred for 2 hours, filtered and washed with cold propan-2-ol (2×550 mL). The solid product was then dried in a vacuum oven at 50° C. to give the title compound (495.9 g, 0.79 mols, 72.9%).

Example 12

The (D)-tartrate salt of N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide was prepared according to method described above for the fumarate salt of Example 9 using N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide and D-tartaric acid. The PXRD peak data are provided hereinbelow.

Preparation 1

8-Benzyl-8-azabicyclo[3.2.1]octan-3-one

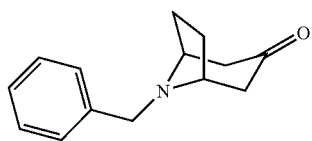

A solution of 2,5-dimethoxytetrahydrofuran (50 g, 378 mmol) in hydrochloric acid (0.025 N, 160 ml) was cooled to 0° C. for 16 hours. Benzylamine hydrochloride (65 g, 453 mmol), ketomalonic acid (55 g, 377 mmol) and an aqueous solution of sodium acetate (300 ml, 0.69 M) were added and the reaction stirred at room temperature for one hour. The mixture was heated to 50° C. for further 90 minutes, then cooled in an ice bath and basified to pH12 with 2N sodium hydroxide solution. The layers were separated and the aqueous phase extracted with ethyl acetate (3×300 ml). The combined organic extracts were washed with water, dried (MgSO$_4$), filtered and evaporated under reduced pressure. The residual brown oil was distilled under reduced pressure (126°/3 mmHg) to afford the title compound as an off-white solid (37.81 g).

LRMS: m/z 216.3 (MH$^+$).

Preparation 2 tert-Butyl 3-oxo-8-azabicyclo[3.2.1]octan-8-carboxylate

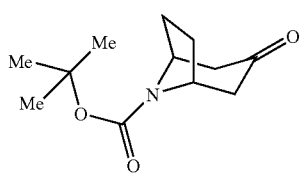

A mixture of 8-benzyl-8-azabicyclo[3.2.1]octan-3-one (15.0 g, 69.7 mmol), di-tert-butyl dicarbonate (18.2 g, 83.4 mmol) and 20% w/w palladium hydroxide on carbon (3.0 g) in ethyl acetate (165 ml) was stirred for 4 hours at room temperature under an atmosphere of hydrogen at 269 kPa. The mixture was filtered through Arbocel® and the solvent removed under reduced pressure. The residue was purified by column chromatography on silica gel using an elution gradient of hexane:ether (100:0 to 50:50) to afford the title compound as a colourless oil which crystallized on standing (16.2 g).

$^1$H NMR (400 MHz, CDCl$_3$): :1.48 (9H, s), 1.60-1.68 (2H, m), 2.00-2.11 (2H, m), 2.26-2.34 (2H, m), 2.48-2.82 (2H, m), 4.35-4.58 (2H, m) ppm.

Preparation 3 tert-Butyl 3-(benzylamino)-endo-8-azabicyclo[3.2.1]octane-8-carboxylate

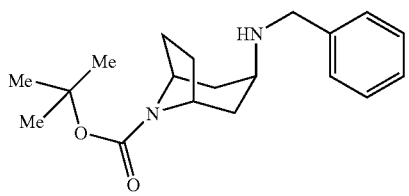

A solution of tert-butyl 3-oxo-8-azabicyclo[3.2.1]octan-8-carboxylate (10.0 g, 44.4 mmol), benzylamine (4.85 ml, 49.7 mmol) and sodium triacetoxyborohydride (14.11 g, 66.6 mmol) was stirred for 16 hours at room temperature in a mixture of glacial acetic acid:dichloromethane (1:9 v/v, 290 ml). The solvents were evaporated under reduced pressure and the residue dissolved in ethyl acetate (200 ml), then washed with saturated aqueous sodium carbonate solution (50 ml) and water (50 ml). The organic solution was dried (MgSO$_4$), filtered and evaporated under reduced pressure. The residue was purified by column chromatography on silica gel using an eluent of dichloromethane:methanol:concentrated aqueous ammonia (98:2:0.25) to afford the title compound as a white solid (7.00 g).

$^1$H NMR (400 MHz, CDCl$_3$): :1.42-1.48 (11H, m), 1.52-1.61 (2H, m), 1.85-2.19 (5H, m), 2.95-3.03 (1H, m), 3.74 (2H, s), 4.03-4.23 (2H, m), 7.20-7.26 (1H, m), 7.26-7.32 (4H, m) ppm.

Preparation 4 tert-Butyl 3-endo-amino-8-azabicyclo[3.2.1]octane-8-carboxylate

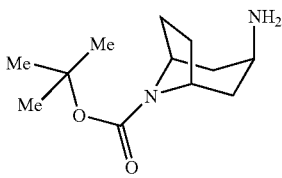

A mixture of tert-butyl 3-(benzylamino)-endo-8-azabicyclo[3.2.1]octane-8-carboxylate (7.00 g, 22.1 mmol), ammonium formate (7.00 g, 111 mmol) and 20% w/w palladium hydroxide on carbon (0.70 g) in ethanol (200 ml) was heated to 50° C., until gas evolution ceased. The cooled mixture was filtered through Arbocel® and the filtrate evaporated under reduced pressure. The residue was purified by column chromatography on silica gel using an elution gradient of dichloromethane:methanol:concentrated aqueous ammonia (98:2:0.25 to 95:5:0.5) to afford the title compound as a colourless oil (4.70 g).

LRMS: m/z 227.2 (MH$^+$).

Preparation 5 tert-Butyl 3-endo-[(3-nitro-4-pyridinyl)amino]-8-azabicyclo[3.2.1]octane-8-carboxylate

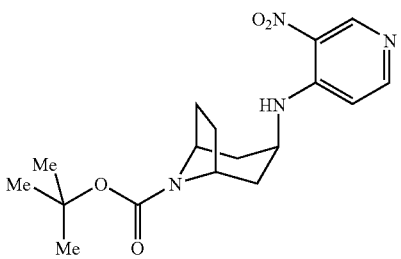

tert-Butyl 3-amino-endo-8-azabicyclo[3.2.1]octane-8-carboxylate (3.0 g, 13.2 mmol), 4-ethoxy-3-nitropyridine hydrochloride (2.7 g, 13.2 mmol) and N-ethyl-N,N-diisopropylamine (1.89 g, 14.6 mmol) were dissolved in 1-methyl-2-pyrrolidinone (5 ml) and heated at 120 C for 18 hours. The cooled reaction mixture was diluted with ethyl acetate (150 ml) and washed with water (3×50 ml), saturated aqueous sodium hydrogen carbonate solution (50 ml) and brine (30 ml). The organic layer was dried (MgSO$_4$) and the solvent removed by evaporation under reduced pressure. This residue was triturated with diethyl ether and filtered to afford the title compound as a yellow solid (1.5 g).

LRMS: m/z 349 (MH$^+$).

Preparation 6

1-endo-(8-Acetyl-8-azabicyclo[3.2.1]oct-3-yl)-2-methyl-1H-imidazo[4,5-c]pyridine

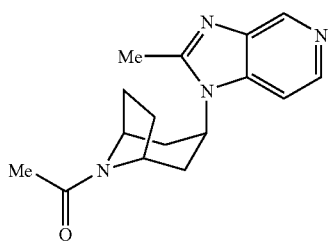

tert-Butyl 3-endo-[(3-nitro-4-pyridinyl)amino]-8-azabicyclo[3.2.1]octane-8-carboxylate (4.40 g, 12.6 mmol) and iron powder (2.11 g, 37.8 mmol) were dissolved in glacial acetic acid (50 ml) and the mixture heated to 60° C. for two hours. Acetic anhydride (8 ml) was then added and the mixture heated to 140° C. for 18 hours. The cooled reaction mixture was filtered through a pad of Arbocel® and solvent was removed under reduced pressure The residue was partitioned between dichloromethane (200 ml) and water (200 ml) and the mixture adjusted to pH 9 with 2 N aqueous sodium hydroxide solution. The mixture was again filtered through a pad of Arbocel® and the organic phase separated. The aqueous layer was extracted with dichloromethane (100 ml) and the combined organic extracts dried (MgSO$_4$). Solvent was evaporated under reduced pressure and the residue triturated with ethyl acetate, filtered and dried (MgSO$_4$) to give the title compound as a white solid (3.27 g).

LRMS: m/z 285 (MH$^+$).

Preparation 7

1-endo-(8-Acetyl-8-azabicyclo[3.2.1]oct-3-yl)-5-benzyl-2-methyl-4,5,6,7-tetrahydro-1H-imidazo[4,5-c]pyridine

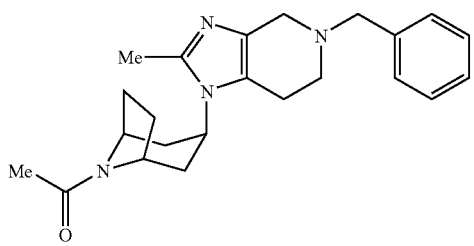

Benzyl bromide (1.78 g, 10.4 mmol) was added to a solution of 1-endo-(8-acetyl-8-azabicyclo[3.2.1]oct-3-yl)-2-methyl-1H-imidazo[4,5-c]pyridine (2.47 g, 8.7 mmol) in ethanol (20 ml) and the mixture stirred at room temperature for 48 hours. The reaction mixture was then cooled to −70 C and sodium borohydride (0.33 g, 8.7 mmol) added portionwise over ten minutes. After one hour at −70 C the reaction mixture was allowed to warm to −40 C then re-cooled to −70 C and further sodium borohydride (0.33 g, 8.7 mmol) added. After an additional hour at −70 C water (10 ml) was added and the reaction mixture allowed to warm to room temperature. The ethanol was evaporated under reduced pressure and the aqueous residue extracted with dichloromethane (3×25 ml). The combined organic extracts were dried (MgSO$_4$) and solvent evaporated under reduced pressure. The residue was purified by flash column chromatography on silica gel eluting with a solvent gradient of ethyl acetate:methanol:diethylamine (100:0:2, by volume, changing to 98:2:2 then 95:5:2). Product containing fractions were evaporated to afford the title compound as a white foam (2.23 g).

LRMS: m/z 379 (MH$^+$).

Preparation 8

1-endo-(8-Azabicyclo[3.2.1]oct-3-yl)-5-benzyl-2-methyl-4,5,6,7-tetrahydro-1H-imidazo[4,5-c]pyridine

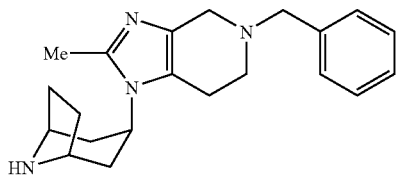

1-endo-(8-Acetyl-8-azabicyclo[3.2.1]oct-3-yl)-5-benzyl-2-methyl-4,5,6,7-tetrahydro-1H-imidazo[4,5-c]pyridine (2.23 g, 5.89 mmol) was dissolved in 6N aqueous hydrochloric acid (30 ml) and heated under reflux for 18 hours. The cooled reaction mixture was adjusted to pH10 by the addition of 2N aqueous sodium hydroxide solution and extracted with dichloromethane (2×50 ml). The combined organic extracts were dried (MgSO$_4$) and solvent evaporated under reduced pressure. The residue was purified by flash column chromatography on silica gel eluting with a solvent gradient of dichloromethane:methanol:diethylamine (100:0:0.5, by volume, changing to 93:7:1). Product containing fractions were evaporated to afford the title compound as a white foam (1.47 g).

LRMS (electrospray): m/z [M+H]$^+$ 337.

Preparation 9 tert-Butyl (1S)-1-(3-fluorophenyl)-3-oxopropylcarbamate

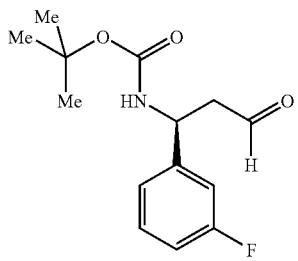

Diisobutylaluminium hydride (1 M in dichloromethane, 39 ml, 39 mmol) was cooled to −78° C. and added dropwise to a solution of methyl (3S)-3-[(tert-butoxycarbonyl)amino]-3-(3-fluorophenyl)propanoate (WO0039125, p 60, preparation 12) (5.4 g, 18.2 mmol) in dichloromethane (100 ml) at −78° C. The reaction was stirred for 30 minutes at −78° C., then methanol (50 ml, pre-cooled to −78° C.) was added. The reaction was stirred for 30 minutes, then 2 N hydrochloric acid (250 ml) added. The bi-phasic mixture was allowed to warm up to room temperature, the layers were separated, and the organic layer was dried (MgSO$_4$), filtered and evaporated under reduced pressure to afford the title compound as a clear, colourless oil, 4.8 g.

LRMS: m/z 268.1 (MH$^+$).

Preparation 10 tert-Butyl (1S)-3-[3-endo-(5-benzyl-2-methyl-4,5,6,7-tetrahydro-1H-imidazo[4,5-c]pyridin-1-yl)-8-azabicyclo[3.2.1]oct-8-yl]-1-(3-fluorophenyl)propyl-carbamate

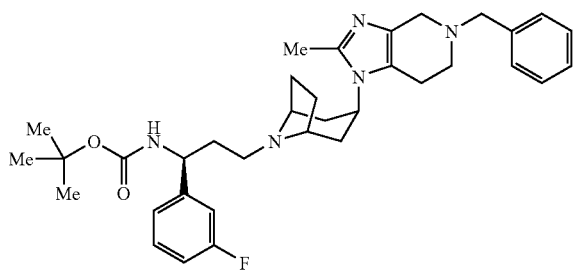

Acetic acid (0.39 g, 6.4 mmol) was added to a stirred solution of 1-endo-(8-azabicyclo[3.2.1]oct-3-yl)-5-benzyl-2-methyl-4,5,6,7-tetrahydro-1H-imidazo[4,5-c]pyridine (2.16 g, 6.4 mmol) and tert-butyl (1S)-1-(3-fluorophenyl)-3-oxopropyl-carbamate (2.06 g, 7.7 mmol) dissolved in dichloromethane (25 ml) under nitrogen at room temperature. Sodium triacetoxyborohydride (1.63 g, 7.7 mmol) was then added and the reaction was held at room temperature for 2 hours. The reaction mixture was partitioned between saturated aqueous sodium hydrogencarbonate solution (50 ml) and dichloromethane (50 ml). The organic phase was removed and the aqueous phase was washed with dichloromethane (50 ml). The combined organic phases were dried (MgSO$_4$) and the solvent was evaporated under reduced pressure. The residue was purified by flash column chromatography on silica gel eluting with a solvent gradient of dichloromethane methanol: concentrated aqueous ammonia (99:1:0.1, by volume, changing to 96:4:0.4). Product containing fractions were evaporated to afford the title compound as a white foam (2.56 g).

LRMS (electrospray): m/z [M+H]$^+$ 588.

Preparation 11 tert-Butyl (1S)-3-[3-endo-(2-methyl-4,5,6,7-tetrahydro-1H-imidazo[4,5-c]pyridin-1-yl)-8-azabicyclo[3.2.1]oct-8-yl]-1-(3-fluorophenyl)propylcarbamate

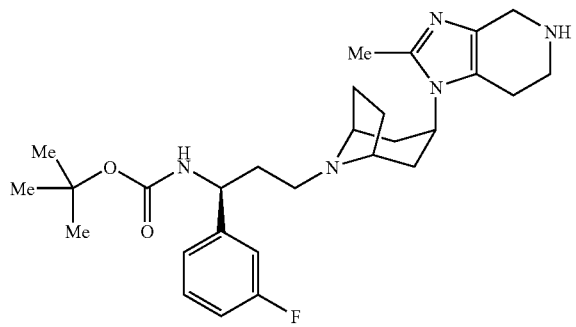

A mixture of tert-butyl (1S)-3-[3-endo-(5-benzyl-2-methyl-4,5,6,7-tetrahydro-1H-imidazo[4,5-c]pyridin-1-yl)-8-azabicyclo[3.2.1]oct-8-yl]-1-(3-fluorophenyl)propylcarbamate (2.55 g, 4.34 mmol), ammonium formate (2.73 g, 43.4 mmol) and 20% w/w palladium hydroxide on carbon (0.25 g) in ethanol (35 ml) was heated to 60° C. After one hour additional ammonium formate (0.63 g, 10.1 mmol) was added and heating continued at 60° C. for a further two hours. The cooled reaction mixture was then filtered through Arbocel® and the filtrate evaporated under reduced pressure. The residue was partitioned between dichloromethane (100 ml) and saturated aqueous sodium hydrogencarbonate solution (50 ml), the organic phase separated and washed with water (30 ml). The organic layer was dried (MgSO$_4$) and solvent evaporated under reduced pressure. The residue was purified by flash column chromatography on silica gel eluting with a solvent gradient of dichloromethane:methanol:concentrated aqueous:ammonia (99:1:0.1 changing to 93:7:1) to afford the title compound as a white foam (1.50 g).

LRMS (electrospray): m/z [M+H]$^+$ 498.

Preparation 12

Methyl 1-endo-(8-{(3S)-3-[(tert-butoxycarbonyl)amino]-3-(3-fluorophenyl)propyl}-8-azabicyclo[3.2.1]oct-3-yl)-2-methyl-4,5,6,7-tetrahydro-1H-imidazo[4,5-c]pyridine-5-carboxylate

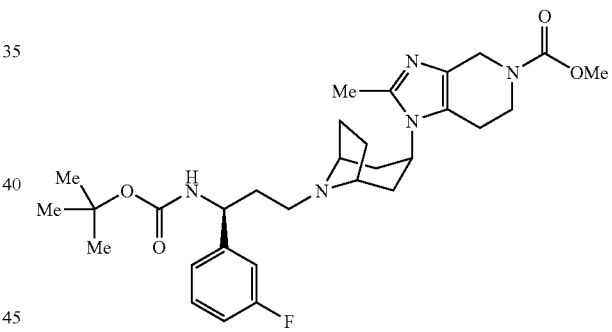

Methyl chloroformate (0.167 g, 1.76 mmol) was added to a solution of tert-butyl (1S)-3-[3-endo-(2-methyl-4,5,6,7-tetrahydro-1H-imidazo[4,5-c]pyridin-1-yl)-8-azabicyclo[3.2.1]oct-8-yl]-1-(3-fluorophenyl)propylcarbamate (0.80 g, 1.60 mmol) in dichloromethane (10 ml) under nitrogen at room temperature. The reaction was stirred at room temperature for 1.5 hours and then washed with saturated aqueous sodium hydrogencarbonate solution (10 ml). The organic phase was removed and the aqueous layer extracted with more dichloromethane (2×10 ml). The combined dichloromethane extracts were dried (MgSO$_4$) and the solvent was removed under reduced pressure. The residue was purified by flash column chromatography on silica gel eluting with a solvent mixture of dichloromethane:methanol:concentrated aqueous ammonia (99:1:0.1 changing to 93:7:1) to afford the title compound as a white foam (0.84 g).

LRMS (electrospray): m/z [M+H]$^+$ 556.

Preparation 13

Methyl 1-endo-{8-[(3S)-3-amino-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate trihydrochloride

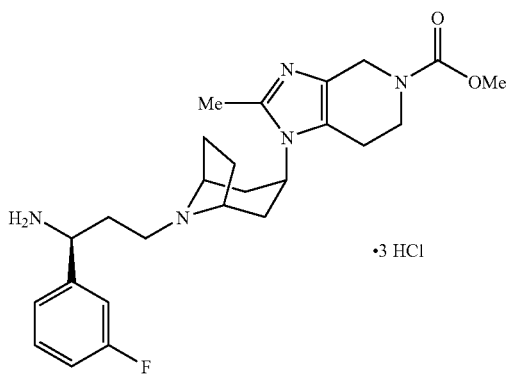

·3 HCl

Hydrogen chloride gas was bubbled through a solution of methyl 1-endo-(8-{(3S)-3-[(tert-butoxycarbonyl)amino]-3-(3-fluorophenyl)propyl}-8-azabicyclo[3.2.1]oct-3-yl)-2-methyl-4,5,6,7-tetrahydro-1H-imidazo[4,5-c]pyridine-5-carboxylate (0.83 g, 1.50 mmol) in dichloromethane (15 ml) at 0° C. until the solution was saturated. The reaction mixture was then allowed to warm to room temperature and stirred for one hour. Solvent was evaporated under reduced pressure and the residue suspended in dichloromethane (10 ml). This process was repeated three times to give the title compound as a white solid (0.82 g).

LRMS (electrospray): m/z [M+H]⁺ 456.

Preparation 14

Methyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate

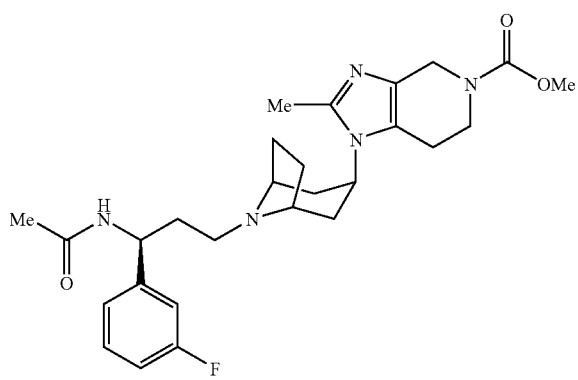

Acetyl chloride (0.062 g, 0.79 mmol) was added to a solution of methyl 1-endo-{8-[(3S)-3-amino-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate trihydrochloride (0.409 g, 0.72 mmol) and triethylamine (0.33 g, 3.25 mmol) dissolved in dichloromethane (10 ml) under nitrogen at room temperature and the reaction mixture stirred for 2 hours. The solution was then washed with water (10 ml), 1 N sodium hydroxide solution (10 ml) and brine (10 ml). The organic phase was separated, dried (MgSO₄) and solvent removed under reduced pressure. The residue was purified by flash column chromatography on silica gel eluting with a solvent gradient of dichloromethane:methanol:concentrated aqueous ammonia (99:1:0.1, by volume, changing to 97:3:0.3). Product containing fractions were evaporated to afford the title compound as a white foam (0.24 g).

LRMS (electrospray): m/z [M+H]⁺ 498.

Preparation 15

N-{(1S)-3-[3-endo-(2-Methyl-4,5,6,7-tetrahydro-1H-imidazo[4,5-c]pyridin-1-yl)-8-azabicyclo[3.2.1]oct-8-yl]-1-(3-fluorophenyl)propyl}acetamide

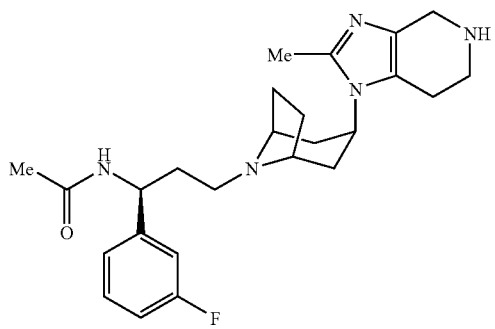

To a stirred solution of Methyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate (13.27 g, 26.7 mmol) in propan-2-ol (80 ml) was added 2M aqueous sodium hydroxide solution (120 ml) and the mixture was heated at reflux for 48 hours. After cooling to room temperature the mixture was extracted with ethyl acetate (2×200 ml). The combined organic components were washed with brine (150 ml), dried (MgSO₄) and concentrated under reduced pressure. The crude product mixture was purified by flash column chromatography eluting with dichloromethane:methanol:concentrated aqueous ammonia (90:10:1 then 80:20:1, by volume) to give the title compound as a white foam (8.54 g, 73%).

LRMS (atmospheric pressure chemical ionisation): m/z [MH⁺] 440

Preparation 16

N-{(1S)-3-[3-endo-(2-Methyl-4,5,6,7-tetrahydro-1H-imidazo[4,5-c]pyridin-1-yl)-8-azabicyclo[3.2.1]oct-8-yl]-1-(3-fluorophenyl)propyl}acetamide

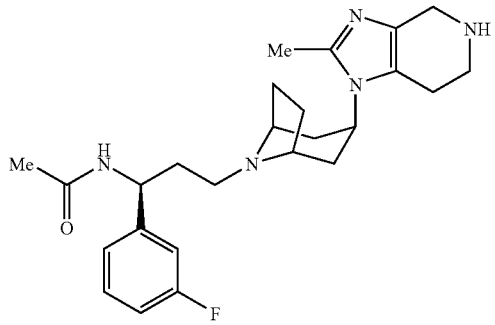

Methyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate (L)-tartrate (WO 03/084954, Example 46) (898 g, 1.39 mol) was added to dichloromethane (4.5 L) and water (4.5 L). Aqueous sodium hydroxide (10M, 450 mL) was then added and the result was stirred for 15 minutes. The two phases were separated and the aqueous layer was extracted with further dichloromethane (2.25 L). The combined organics were then concentrated and the resulting oil was dissolved in propan-2-ol (4.5 L). Aqueous sodium hydroxide (2M, 6.93 L, 13.9 mol) was then added and the biphasic mixture was heated at reflux for 65 hours. After cooling to room temperature, the phases were separated and the aqueous layer was extracted with ethyl acetate (4.5 L). The combined organics were then washed with saturated aqueous sodium chloride (4.5 L) and concentrated under vacuum. The residue was diluted with ethyl acetate (9 L) and concentrated once again under vacuum. Finally, more ethyl acetate (4.5 L) was added and the resulting slurry was stirred at 0-5° C. for 1 hour, filtered and washed with cold ethyl acetate (2×450 mL). The solid product was then dried in a vacuum oven at 40° C. to afford the title compound (547.2 g, 1.24 mol, 89.8%). The LRMS data for the title compound was identical to the title compound of Preparation 15.

Biological Data

The ability of the compounds of formula (I) and their pharmaceutically acceptable salts, solvates and derivatives to modulate chemokine receptor activity is demonstrated by methodology known in the art, such as by using the assay for CCR5 binding following procedures disclosed in Combadiere et al., J. Leukoc. Biol., 60, 147-52 (1996); and/or by using the intracellular calcium mobilisation assays as described by the same authors. Cell lines expressing the receptor of interest include those naturally expressing the receptor, such as PM-1, or IL-2 stimulated peripheral blood lymphocytes (PBL), or a cell engineered to express a recombinant receptor, such as CHO, 300.19, L1.2 or HEK-293.

The compound of Example 4 when tested using the assay for CCR5 binding according to Combadiere et al (ibid) had $IC_{50}$ values of 7.5 nM (MIP-1α), 7.3 nM (MIP-1β) and 6.7 nM (RANTES).

The compound of Example 5 when tested using the assay for CCR5 binding according to Combadiere et al had $IC_{50}$ values of 2.7 nM (MIP-1α), 2.4 nM (MIP-1β) and 1.9 nM (RANTES).

All the Examples, when tested using the assay for intracellular calcium mobilisation according to Combadiere et al (ibid) were potent antagonists with $IC_{50}$ values of less than 100 nM (MIP-1β).

The pharmacological activity of the compounds of formula (I) and their pharmaceutically acceptable salts, solvates and derivatives is further demonstrated using a gp160 induced cell-cell fusion assay to determine the $IC_{50}$ values of compounds against HIV-1 fusion. The gp160 induced cell-cell fusion assay uses a HeLa P4 cell line and a CHO-Tat10 cell line.

The HeLa P4 cell line expresses CCR5 and CD4 and has been transfected with HIV-1 LTR-β-Galactosidase. The media for this cell line is Dulbecco modified eagle's medium (D-MEM) (without L-glutamine) containing 10% foetal calf serum (FCS), 2 mM L-glutamine penicillin/streptomycin (Pen/Strep; 100 U/mL penicillin+10 mg/mL streptomycin), and 1 µg/ml puromycin.

The CHO cell line is a Tat (transcriptional trans activator)-expressing clone from a CHO JRR17.1 cell line that has been transfected with pTat puro plasmid. The media for this cell line is rich medium for mammalian cell culture originally developed at Roswell Park Memorial Institute RPMI1640 (without L-glutamine) containing 10% FCS, 2 mM L-glutamine, 0.5 mg/ml Hygromycin B and 12 µg/ml puromycin. The CHO JRR17.1 line expresses gp160 (JRFL) and is a clone that has been selected for its ability to fuse with a CCR5/CD4 expressing cell line.

Upon cell fusion, Tat present in the CHO cell is able to transactivate the HIV-1 long terminal repeat (LTR) present in the HeLa cell leading to the expression of the β-Galactosidase enzyme. This expression is then measured using a Fluor Ace™ β-Galactosidase assay reporter kit (Bio-Rad cat no. 170-3150). This kit is a quantitative fluorescent assay that determines the level of expression of β-galactosidase using 4-methylumbelliferul-galactopyranoside (MUG) as substrate. β-Galactosidase hydrolyses the fluorogenic substrate resulting in release of the fluorescent molecule 4-methylumbelliferone (4 MU). Fluorescence of 4-methylumbelliferone is then measured on a fluorometer using an excitation wavelength of 360 nm and emission wavelength of 460 nm.

Compounds that inhibit fusion will give rise to a reduced signal and, following solubilisation in an appropriate solvent and dilution in culture medium, a dose-response curve for each compound can be used to calculate $IC_{50}$ values.

All the compounds of the Examples of the invention have $IC_{50}$ values, according to the above method, of less than 10 nM. The compounds of Examples 1 and 5 have, respectively, $IC_{50}$ values of 130 and 120 pm.

Powder X-Ray Diffraction (PXRD) Data

All PXRD patterns were collected on a Bruker D5000 Powder Diffractometer over the 2-theta angular range 2-550 with a 0.02° step size. The specimen was rotated whilst being irradiated with copper K-alpha1 X-rays (Wavelength=1.5046 Angstroms) filtered with a graphite monochromator (λ=0.15405 nm) with the X-ray tube operated at 40 kV/40 mA. The diffractometer was calibrated with a standard quartz sample before and after the data collection for each sample.

The main peaks (in degrees 2-theta) of the PXRD patterns for Examples 10, 11 and 12 are illustrated in the following tables:

TABLE 1

The PXRD peak data for N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide.

| Angle (° 2-theta) | Intensity (%) |
|---|---|
| 8.1 | 90.5 |
| 9.0 | 20.9 |
| 9.8 | 12.8 |
| 10.7 | 89.1 |
| 11.3 | 39.8 |
| 12.3 | 100.0 |
| 13.1 | 24.2 |
| 14.1 | 67.3 |
| 14.5 | 19.4 |
| 15.8 | 55.4 |
| 16.3 | 49.9 |
| 16.6 | 48.5 |
| 17.0 | 49.6 |
| 17.8 | 80.7 |
| 18.3 | 67.4 |
| 18.6 | 43.6 |
| 18.9 | 48.3 |
| 19.9 | 39.2 |
| 20.5 | 48.3 |
| 21.0 | 43.8 |
| 21.5 | 50.4 |
| 22.5 | 51.4 |
| 23.1 | 46.1 |
| 23.3 | 54.9 |
| 24.1 | 35.8 |
| 24.8 | 29.5 |
| 25.4 | 38.0 |
| 25.6 | 34.6 |
| 26.2 | 43.0 |
| 27.0 | 21.3 |
| 27.9 | 28.6 |
| 28.9 | 25.5 |
| 29.4 | 24.6 |
| 30.0 | 21.7 |
| 35.9 | 18.9 |

TABLE 2

The PXRD peak data for N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide fumarate.

| Angle (° 2-theta) | Intensity (%) |
|---|---|
| 6.7 | 38.6 |
| 10.0 | 34.1 |
| 10.2 | 17.7 |
| 10.4 | 36.2 |
| 10.9 | 16.2 |
| 12.8 | 13.1 |
| 13.6 | 10.1 |
| 16.7 | 100.0 |
| 17.0 | 16.1 |
| 17.6 | 32.0 |
| 18.2 | 31.1 |
| 18.4 | 77.8 |
| 19.1 | 18.2 |
| 19.6 | 77.8 |
| 20.1 | 10.2 |
| 20.6 | 65.2 |
| 20.8 | 23.4 |
| 21.1 | 42.3 |
| 22.2 | 20.2 |
| 22.6 | 24.1 |
| 22.9 | 37.0 |
| 23.4 | 12.3 |
| 24.8 | 14.3 |
| 25.0 | 12.9 |
| 25.5 | 10.1 |
| 26.7 | 17.6 |
| 28.3 | 24.1 |
| 28.6 | 13.6 |
| 29.0 | 10.1 |
| 29.7 | 19.0 |
| 30.0 | 12.8 |
| 31.0 | 11.0 |
| 33.0 | 15.2 |
| 34.6 | 13.2 |

TABLE 3

The PXRD peak data for N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide(D)-tartrate.

| Angle (° 2-theta) | Intensity (%) |
|---|---|
| 5.0 | 12.5 |
| 6.9 | 59.6 |
| 9.0 | 17.1 |
| 9.2 | 10.9 |
| 10.0 | 14.6 |
| 10.4 | 17.3 |
| 11.0 | 15.1 |
| 12.4 | 14.5 |
| 13.6 | 12.5 |
| 14.4 | 13.7 |
| 14.8 | 10.1 |
| 16.4 | 41.3 |
| 16.6 | 42.4 |
| 17.1 | 100.0 |
| 18.0 | 65.1 |
| 18.5 | 50.0 |
| 19.0 | 27.1 |
| 19.5 | 23.9 |
| 20.0 | 31.5 |
| 20.8 | 30.6 |
| 21.2 | 42.2 |
| 21.4 | 39.0 |
| 22.5 | 41.6 |
| 25.0 | 15.8 |
| 28.0 | 21.2 |
| 29.1 | 25.7 |
| 29.7 | 21.6 |
| 30.9 | 17.2 |
| 32.1 | 21.0 |

A PXRD pattern simulation for N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide fumarate involving 2-theta angles, d spacings and relative intensities was calculated from its single crystal structure using the "Reflex Powder Diffraction" module of Accelrys Materials Studio™ [version 2.2]. Pertinent simulation parameters were:

Wavelength=1.540562 Å (Cu K)

Polarisation Factor=0.5

Pseudo-Voigt Profile (U=0.01, V=−0.001, W=0.002)

The main peaks (in degrees 2-theta) of the simulated PXRD pattern for N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide fumarate are listed in table 4.

TABLE 4

Simulated PXRD peak data for N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide fumarate.

| Angle (° 2-theta) | Intensity (%) |
|---|---|
| 6.7 | 59.4 |
| 10.0 | 64.5 |
| 10.5 | 67.7 |
| 11.0 | 28.8 |
| 12.8 | 12.7 |
| 13.6 | 17.0 |
| 16.7 | 93.8 |
| 17.0 | 19.6 |
| 17.7 | 32.3 |
| 18.2 | 30.0 |
| 18.5 | 100.0 |
| 19.1 | 15.4 |
| 19.6 | 98.3 |
| 20.6 | 56.8 |
| 21.1 | 45.1 |
| 22.2 | 13.8 |
| 22.5 | 16.1 |
| 22.9 | 39.1 |
| 23.4 | 10.0 |
| 26.8 | 11.2 |
| 28.3 | 15.5 |
| 28.6 | 10.8 |
| 29.7 | 14.1 |
| 30.0 | 11.6 |

Differential Scanning Calorimetry Data

All DSC data were collected on a Perkin Elmer PYRIS Diamond DSC with autosampler, with a gas flow of nitrogen. Samples were placed in 50 μl aluminium pans with holes and lids and heated from 10-300° C. at a rate of 20° C. min$^{-1}$.

N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide Sample size 3.016 mg Endotherm peak at 118° C.-melt N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide fumarate Sample size 2.905 mg Endotherm peak at 219° C.-melt Endotherm event at 228° C.

Exotherm event at 246° C.

N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide(D)-tartrate Sample size 2.979 mg Endotherm peak at 217° C.-melt

I claim:

1. A method of treating a mammal suffering from a disorder in which the modulation of CCR5 receptors is implicated, comprising administering to said mammal a compound of formula (I)

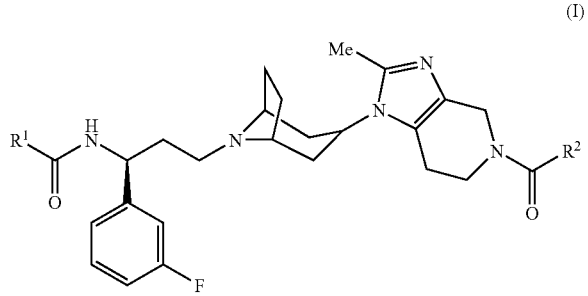

(I)

or a pharmaceutically acceptable salt or a hydrate thereof wherein:

$R^1$ is $C_1$-$C_6$ alkyl; and $R^2$ is $C_1$-$C_6$ alkyl or $C_3$-$C_7$cycloalkyl, wherein said $C_1$-$C_6$ alkyl is optionally substituted by $CF_3$ and wherein said disorder is HIV, a retroviral infection related to HIV, AIDS, HBV, HCV, plague, pox virus, toxoplasmosis, mycobacterium, trypanosomal, pneumonia, or cytosporidiosis.

2. A method according to claim 1 wherein said disorder is HIV, a retroviral infection related to HIV, or AIDS.

3. A method according to claim 1 wherein said disorder is HBV, HCV, plague, pox virus, toxoplasmosis, mycobacterium, trypanosomal, pneumonia, or cytosporidiosis.

4. The method according to claim 1 wherein $R^1$ is $C_1$-$C_4$ alkyl.

5. The method according to claim 4 wherein $R^1$ is methyl.

6. The method according to claim 1 wherein $R^2$ is $C_1$-$C_4$ alkyl optionally substituted by $CF_3$.

7. The method according to claim 6 wherein $R^2$ is methyl, ethyl or i-propyl.

8. The method according to claim 1 wherein $R^2$ is cyclopropyl or cyclobutyl.

9. The method according to claim 1 wherein the compound of formula (I) is selected from the group consisting of:

N-{(1S)-3-[3-endo-(5-Acetyl-2-methyl-4,5,6,7-tetrahydro-1H-imidazo[4,5-c]pyridin-1-yl)-8-azabicyclo[3.2.1]oct-8-yl]-1-(-3-fluorophenyl)propyl}acetamide;

N-{(1S)-3-[3-endo-(5-Cyclobutanecarbonyl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide;

N-{(1S)-3-[3-endo-(5-Cyclopropanecarbonyl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide;

N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide;

N-{(1S)-3-[3-endo-(2-Methyl-5-propionyl-4,5,6,7-tetrahydro-1H-imidazo[4,5-c]pyridin-1-yl)-8-azabicyclo[3.2.1]oct-8-yl]-1-(3-fluorophenyl)propyl}acetamide;

N-{(1S)-3-[3-endo-(5-Butyryl-2-methyl-4,5,6,7-tetrahydro-1-H-imidazo[4,5-c]pyridin-1-yl)-8-azabicyclo[3.2.1]oct-8-yl]-1-(3-fluorophenyl)propyl}acetamide;

N-{(1S)-3-[3-endo-(2-Methyl-5-(2,2-dimethyl-propionyl-)-4,5,6,7-tetrahydro-1H-imidazo[4,5-c]pyridin-1-yl)-8-azabicyclo[3.2.1]oct-     -8-yl]-1-(3-fluorophenyl)propyl}acetamide;

N-{(1S)-3-[3-endo-(2-Methyl-5-(-3,3,3-trifluoro-propionyl-)-4,5,6,7-tetrahydro-1H-imidazo[4,5-c]pyridin-1-yl)-8-azabicyclo[3.2.1]oct-8-yl]-1-(3-fluorophenyl)propyl}acetamide; or a pharmaceutically acceptable salt of said compound.

10. A method of treating a mammal suffering from HIV comprising administering to said mammal an effective amount of N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide or a pharmaceutically acceptable salt or a hydrate thereof.

* * * * *